US007045576B2

(12) United States Patent
Balasubramanian et al.

(10) Patent No.: US 7,045,576 B2
(45) Date of Patent: May 16, 2006

(54) ADJUVANTS AND COPOLYMER COMPOSITIONS

(75) Inventors: Mannarsamy Balasubramanian, Roswell, GA (US); Mark Joseph Newman, Duluth, GA (US); R. Martin Emanuele, Alpharetta, GA (US); Carlos A. Rivera-Marrero, Norcross, GA (US); Charles William Todd, Lawrenceville, GA (US); Robert Newton Brey, III, Alpharetta, GA (US)

(73) Assignee: Cytrx Corporation, Los Angeles, CA (US)

( * ) Notice: Subject to any disclaimer, the term of this patent is extended or adjusted under 35 U.S.C. 154(b) by 0 days.

(21) Appl. No.: 10/888,357

(22) Filed: Jul. 9, 2004

(65) Prior Publication Data

US 2005/0070670 A1    Mar. 31, 2005

Related U.S. Application Data

(60) Division of application No. 10/115,332, filed on Apr. 2, 2002, now Pat. No. 6,844,001, which is a continuation of application No. 09/532,345, filed on Mar. 21, 2000, now Pat. No. 6,416,947, which is a continuation of application No. 09/221,339, filed on Dec. 28, 1998, now Pat. No. 6,149,922, which is a continuation of application No. 08/513,162, filed on Aug. 9, 1995, now Pat. No. 6,086,899, which is a continuation-in-part of application No. 08/292,814, filed on Aug. 9, 1994, now abandoned.

(51) Int. Cl.
*C08L 71/02* (2006.01)

(52) U.S. Cl. ............... 525/118; 525/162; 525/173; 525/187

(58) Field of Classification Search ............... 525/118, 525/162, 173, 187; 528/421
See application file for complete search history.

(56) References Cited

U.S. PATENT DOCUMENTS

| | | | |
|---|---|---|---|
| 2,674,619 A | 4/1954 | Lundsted | |
| 3,393,243 A | 7/1968 | Cuscurida | |
| 4,764,567 A | 8/1988 | Ott | |
| 4,772,466 A | 9/1988 | Allison et al. | |
| 4,902,834 A | 2/1990 | Otten | |
| 5,313,000 A | 5/1994 | Stewart | |
| 5,523,492 A | 6/1996 | Emanuele et al. | |
| 5,554,372 A | 9/1996 | Hunter | |
| 5,567,859 A | 10/1996 | Emanuele et al. | |
| 5,674,911 A | 10/1997 | Emanuele et al. | |
| 6,086,899 A * | 7/2000 | Balasubramanian et al. | 424/280.1 |

FOREIGN PATENT DOCUMENTS

| | | |
|---|---|---|
| EP | 0121752 | 10/1984 |
| EP | 0135376 | 3/1985 |
| EP | 0 283148 A2 | 9/1988 |
| WO | WO 90/15092 | 12/1990 |
| WO | WO 92/16484 | 10/1992 |
| WO | WO 95/10265 | 4/1995 |

OTHER PUBLICATIONS

Aida, et al., "Synthesis of Propylane Oxide-Ehylene Oxide Block Copolyeners with Controlled Moleuclar Weight, Using Metalloporphyin as a Catalyst," *Maluonol, Chem. Rapid Comm.* vol. 1, pp. 877-880 (1980).

Hunter, et al., "The Adjuvant Activity of Nonlonic Black Polymer Surfactant. I. The Role of Hydrophile-Lipophile Balance." *J. Immunol.*, vol. 127, No. 3, pp. 1244-1250 (1981).

Hunter, et al. "The Adjuvant Activity of Noalonic Block Polymer Surfactant. III. Characterization of Selected Biologically Active Surfaces," *Scand. J. Immunol.*, vol. 23, pp. 287-300 (1986).

Hunter, et al., "Adjuvant activity of non-ionic block copolymars. IV. Effect of molecular weight and formulation on litre and lactype of antibody." *Vaccine*, vol. 9, pp. 250-256 (Apr. 1991).

Lopez, et al., "Polymerization of Some Ondranes Using the Diphenylzinc-Butanone System in Benzane at 80° C," *Polymer International*, vol. 24, No. 2, pp. 105-112 (1991).

Lowe, A.J., et al., "Some Effects of Molecular Structure on the Production of Flexible Urethane Foam," *J. Cellular Plastics*, vol. 1 (1), pp. 121-131 (1965).

Malkemus, "Production of Alkylens Oxide Derivatives," *The Journal of the American Oil Chemists' Society*, vol. 33, pp. 571-574 (1956).

Newman, et al., "Increasing the Immunogenicity of a Trivalent Influenza Virus Vaccine with Adjuvant-active Nonionic Block Copolymers for Potential Use in the Elderly," *Mechanisms of Aging and Development*, vol. 93, pp. 189-203 (1997).

Reisch, et al., "MHW Polyether Polyols Yield Improved PU Cast Elastomers and Sealants," *Elastomarics*, pp. 18-23 (1991).

Reisch, et al., "Polyurethane Sealants and Cast Elastomers with Superior Physical Properties," $33_{rd}$ *Annual Polurethane Technical/Marketing Conference*, pp. 368-373 (Sep. 30-Oct. 3, 1990).

Schick, M.J., "Nonionic Surfactants," Solvent Properties of Surfactant Solutions, vol. 2, pp. 10-13, 20-23, 26-29.

(Continued)

*Primary Examiner*—James J. Seidleck
*Assistant Examiner*—Olga Asinovsky
(74) *Attorney, Agent, or Firm*—Kilpatrick Stockton LLP

(57) ABSTRACT

The present invention comprises novel polyoxyethylene/polyoxypropylene block copolymers compositions and compounds. The compositions comprise block copolymers that are useful in gene therapy methods.

6 Claims, 32 Drawing Sheets

OTHER PUBLICATIONS

Schuchardt, et al., "Preparation of High Molecular Weight Polyols Using Double Metal Cyanide Catalysts," 32nd *Annual Annual Polyurethane Technical/Marketing Conference*, pp. 360-364 (Oct. 1-4, 1989).

Shachat, et al., "Mechanism of Ethylene Oxide Condensation," *Nonionic Surfectants*, vol. 2, pp. 10-29 (1987).

Smith, et al., "Thermoplastic Polyurethane Elastomers Made from High Molecular Weight POLY-L™ Polyola," *Polyuelhanes World Congress*, 1991, pp. 313-318 (Sep. 24-26, 1991).

Todd, et al, "Development of an Adjuvant-Active Nonionic Block Copolymer for use in Oil-Free Subunit Vaccine Formulations," *Vaccine*, vol. 15, No. 5, pp. 564-570 (1997).

Triozzi, et al., "Effects of a β-Human Chorionic Gonadotropin Subunit Immunogen Administered in Aqueous Solution with a Novel Nonionic Block Copolymer Adjuvant in Patients with Advanced Cancer," *Clinical Cancer Research*, vol. 3, pp. 2355-2362 (1997).

Wu, et al., "New Catalyst Systems of Rare Earth Actytaoetonate/AIEI$_3$-1/2 H$_2$O for Polymerization of Propylane Oxide," *J. Polymer Sci.*, vol. 26, pp. 1995-1997 (1999).

The Pluronic Grid, 6th Ed., Wyandolte Chemicals Corp., Wyandotte, Michigan (1988).

"The Synthasis and Properties of Block Copolymer Polyol Surfectants," *Block and Graft Copolymerization*, R.J. Ceresa, eds, John Wiley & Sons (London), pp. 13-21 (1976).

* cited by examiner

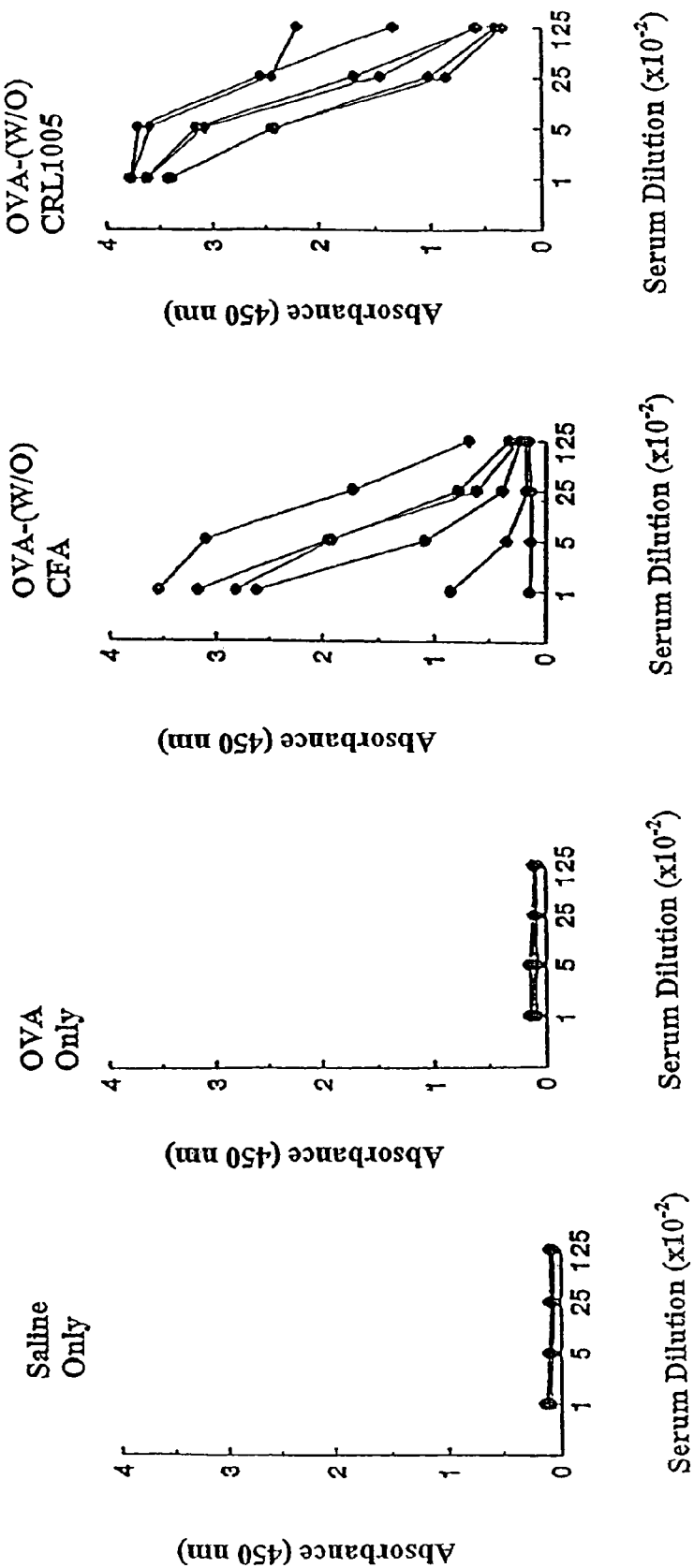

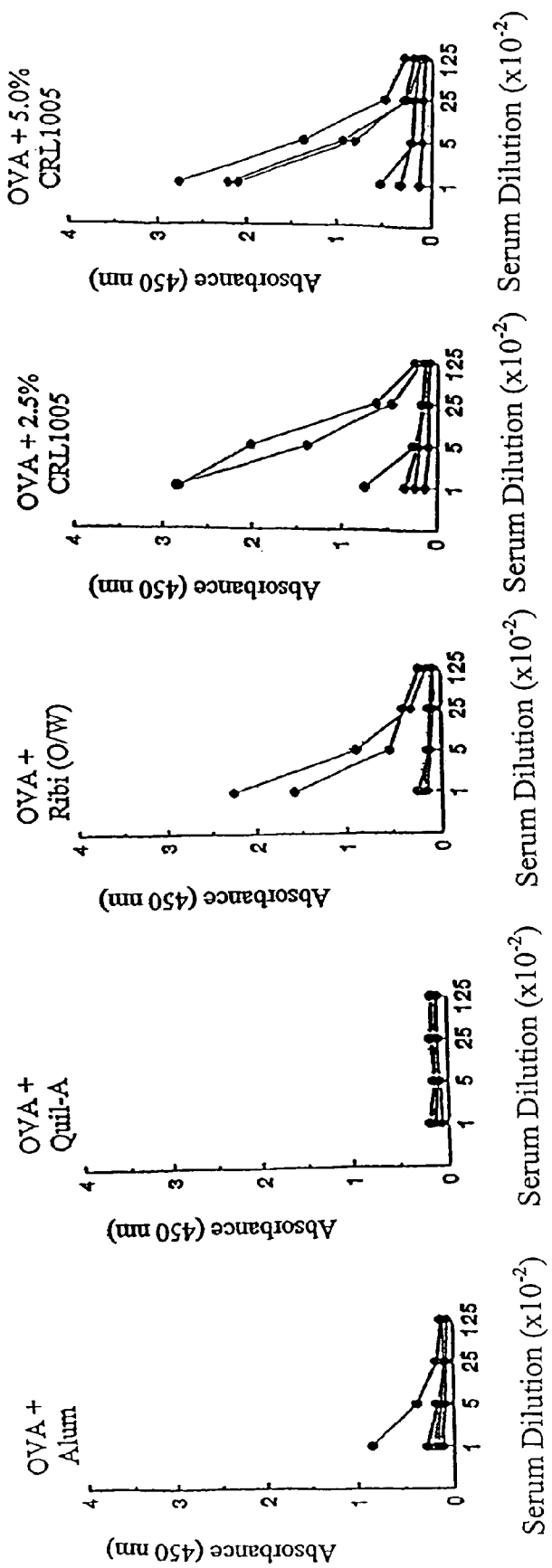

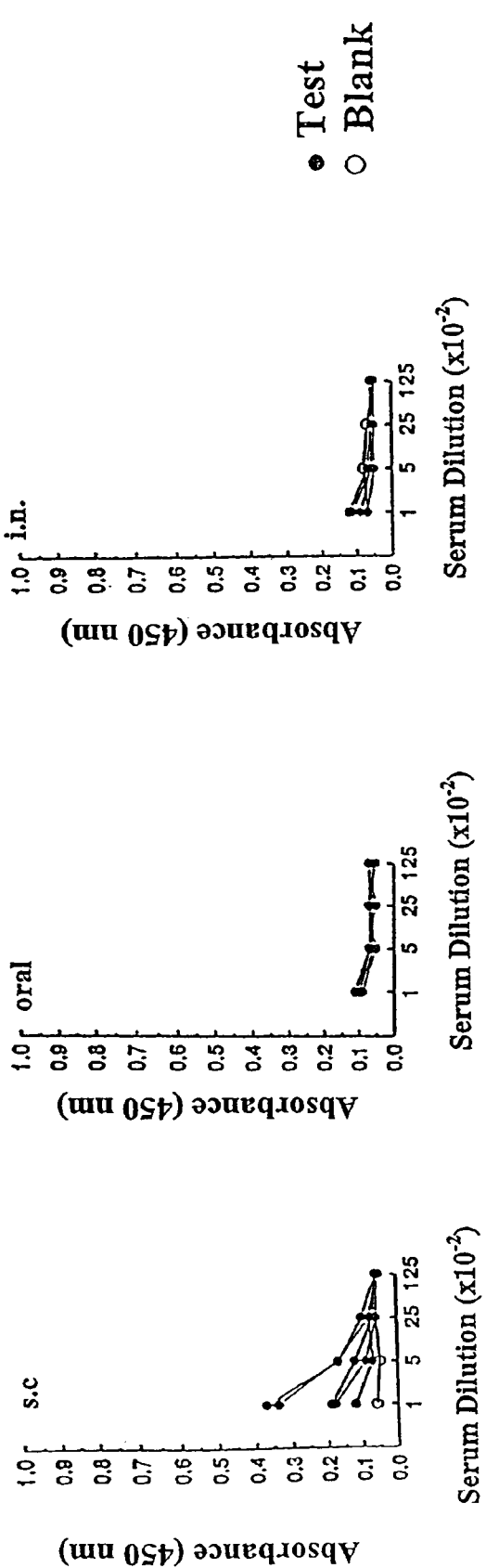

ADJUVANTS AND COPOLYMER COMPOSITIONS

CROSS-REFERENCE TO RELATED APPLICATIONS

The present application is a divisional application of U.S. application Ser. No. 10/115,332, filed Apr. 2, 2002, now U.S. Pat. No. 6,844,001, which is a continuation of U.S. application Ser. No. 09/532,345, filed Mar. 21, 2000, now U.S. Pat. No. 6,416,947, which is a continuation of U.S. application Ser. No. 09/221,339, filed Dec. 28, 1998, now U.S. Pat. No. 6,149,922, which is a continuation of U.S. application Ser. No. 08/513,162, filed Aug. 9, 1995, now U.S. Pat. No. 6,086,899, which is a continuation-in-part of U.S. application Ser. No. 08/292,814, filed Aug. 9, 1994, now abandoned; each of which is incorporated herein by reference.

TECHNICAL FIELD

The present invention comprises methods for synthesizing novel high molecular weight nonionic copolymers. The present invention also comprises high molecular weight nonionic copolymers that are useful as surfactants and have desirable effects on living cells and organisms, including use as adjuvants in vaccines for humans and animals to augment or otherwise modify vaccine induced immune responses.

BACKGROUND OF THE INVENTION

Nonionic block copolymers comprising blocks of polyoxypropylene and polyoxyethylene have been synthesized and shown to have variable uses depending the molecular size of the hydrophobic and hydrophilic regions. The commercially available nonionic copolymers are molecules that have low molecular weight hydrophobic polyoxypropylene regions with varying percentages of total molecular weight hydrophilic regions attached. These nonionic copolymers are prepared by the sequential addition of two or more alkylene oxides to a low molecular weight water-soluble organic compound containing one or more active hydrogen atoms.

The prior art methods of synthesizing nonionic block copolymers includes the sequential addition first of propylene oxide units and then ethylene oxide units to a low molecular weight, water-soluble organic initiator compound, such as propylene glycol. The oxyalkylation steps are carried out in the presence of an alkaline catalyst such as sodium or potassium hydroxide. The alkaline catalyst is then neutralized and removed from the final product. The size of copolymers made using this technique are limited to molecules with hydrophobic molecular weights of approximately 4000, 10 to 80% of the total molecule consisting of ethylene oxide.

Other nonionic copolymers have been synthesized using nitrogen containing molecules as the base molecule. The condensation of propylene oxide with a nitrogen-containing reactive hydrogen compound and the subsequent condensation of ethylene oxide therewith were carried out in the known manner for condensing alkylene oxides with reactive hydrogen compounds. The process is normally carried out at elevated temperatures and pressures in the presence sodium hydroxide, potassium hydroxide, sodium alkoxide, quaternary ammonium bases and the like. The condensation reactions can also be carried out in the presence of an acid catalyst. The manipulative steps will vary to some extent depending upon the normal physical state of the reactive hydrogen compound.

Although nonionic block copolymers can be synthesized with low molecular weight hydrophobic regions, using conventional alkali catalyzed polymerization methods, no one has been able to synthesize nonionic copolymers with high molecular weight hydrophobic regions. Problems with the synthesis of high molecular weight nonionic polyoxyethylene/polyoxypropylene copolymers, especially with high molecular weight hydrophobe regions, include a high degree of unsaturation and a high degree of premature chain termination resulting in a distribution of components with low molecular weight chains along with the distribution of components with desirable high molecular weight chains. Using prior art methods of producing polyoxyethylene/polyoxypropylene block copolymers results in an unacceptable variety of polymer sizes and an unacceptably high degree of unsaturation in the polymer. This is especially undesirable when the copolymers are to be used in biological application.

One of the needs of the medical industry is for compounds that modulate the immune response in various ways. In addition, compounds are needed to facilitate gene transfer in cells. For example, over the past decade, the emergence of methods of gene transfer to mammalian cells has prompted enormous interest in the development of gene-based technologies for the treatment of human disease. Current gene therapy technology has focused primarily on the use of viral and retroviral vectors which provide highly efficient transduction and high levels of gene expression in vivo. The most studied are retroviral vectors, replication-defective murine retroviruses, which require specialized "packaging" cell lines for their replication. Retroviral vectors integrate into chromosomes of dividing cells leading to stable expression of the integrated gene. Also, replication-defective adenoviral and adeno-associated viral vectors have been extensively utilized. These vectors have the advantage of efficiently transducing non-dividing cells, generally do not integrate into the host cell genome, and result in high levels of transient gene expression. However, the use of viral methods of gene transfer for human therapy has raised safety concerns mainly due to the potential of replication-defective viral vectors to become replication-competent and therefore infectious (reviewed by Mulligan, 1993).

An alternative to viral gene transfer has been the use of non-viral methods such as: cationic liposomes, delivery of ligand-DNA complexes by receptor-mediated endocytosis, DNA coated microprojectiles and naked DNA. Liposome-mediated gene transfer has been utilized extensively in in vitro transfection studies but its application for in vivo gene delivery has been limited. The main disadvantage of these methods is that only transient gene expression is achieved and thus repeated administrations would be necessary if continued gene expression were needed.

Recent studies have focused in the use of naked DNA for genetic immunization. It has been shown that intramuscular inoculation of BALB/c mice with a high concentration of plasmid DNA encoding influenza A nucleoprotein results in the generation of specific CTL responses and protection from a challenge infection of influenza A virus (Ulmer, J. B., et al. (1993) Heterologous protection against influenza by injection of DNA encoding a viral protein. *Science* 259, 1745–1749). Successful genetic vaccination against influenza virus has also being obtained by intradermal immunization with naked DNA (Raz, E. et al., (1994) Intradermal gene immunization: The possible role of DNA uptake in the induction of cellular immunity to viruses. *PNAS* 91, 9519–9523). Although successful immunization has been achieved using DNA alone, other more efficient methods of DNA delivery such as the use of DNA-coated microprojectiles are being explored (Vahlsing, H. L., et al. (1994) Immunization with plasmid DNA using a pneumatic gun. *J. Immunol. Meth.* 175, 11–22).

What is needed is a composition of polyoxyethylene/polyoxypropylene block copolymers with narrow molecular weight distribution and polyoxypropylene hydrophobic block molecular weight higher than approximately 7000. Further, what is needed is a method for synthesizing nonionic polyoxyethylene/polyoxypropylene copolymers with a narrow molecular weight distribution and high molecular weight polyoxypropylene hydrophobe. These copolymers should also have enhanced activity as adjuvants, permitting vaccination with lower amounts of antigens such as viral proteins, and display lower toxicity than conventional adjuvants. Also needed are compounds that can facilitate the transfer of genes to cells.

SUMMARY OF THE INVENTION

In accordance with the present invention, a new class of polyoxyethylene/polyoxypropylene copolymers, useful as surfactants and adjuvants and capable of affecting biological systems is provided. The present invention provides a synthetic method and a resulting composition for nonionic block polyoxyethylene polyoxypropylene copolymers with a molecular weight of the hydrophobic region that is much higher than block copolymers currently available. The compositions are particularly useful as surfactants and as adjuvants in vaccines and gene therapy etc. The superior adjuvant properties of the composition facilitate vaccination with lower amounts of antigen.

The biologically-active copolymer of the present invention comprises a block copolymer of polyoxyethylene (POE), which is hydrophilic, and polyoxypropylene (POP) which is hydrophobic. The block copolymer is built on a propylene glycol initiator. In a preferred embodiment of the biologically-active copolymers of the present invention, the block copolymers that comprise the biologically-active copolymers of the present invention have the following general formulas:

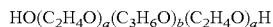

$$HO(C_2H_4O)_a(C_3H_6O)_b(C_2H_4O)_aH$$

wherein "b" represents a number such that the molecular weight of the polyoxypropylene hydrophobe ($C_3H_6O$) is between approximately 7,000 and 20,000 Daltons and "a" represents a number such that the percentage of polyoxyethylene hydrophile ($C_2H_4O$) is between approximately 1% and 40% by weight.

According to the present invention, the copolymer is synthesized using propylene glycol as the initiating molecule. Cesium hydroxide ($CsOH.H_2O$) is the catalyst, usually used in a mole ratio of 1:2 to 1:8 with the initiating molecule. Under reduced pressure and elevated temperatures, the propylene oxide is added by rate limiting vapor phase addition to the reaction mixture until the molecular weight of the added polyoxypropylene is at least 8000 Daltons depending upon the size of the desired final product. Once the desired molecular weight is achieved, the addition of propylene oxide is halted. Ethylene oxide is then introduced by vapor phase addition to the reaction mixture and allowed to add to the polypropylene termini of the molecule until the polyethylene portion of the molecule is grown to approximately 2% to 40% of the total molecular weight of the molecule. The resulting nonionic block copolymer molecule has a high molecular weight hydrophobic region, the polyoxypropylene block, flanked by a low molecular weight hydrophilic region, the polyoxyethylene region.

Although the reaction of propylene oxide with the reactive hydrogen compound is typically carried out by simply heating a mixture of the reactants under pressure at a sufficiently high temperature, this method is not useful as the temperatures and pressure required are excessive, control of the reaction is difficult, and the amount of low molecular weight fraction is significantly high. In addition, the material resulting from such a method is extremely heterogeneous and polydisperse. According to the present invention, by adding the propylene oxide to the reaction vessel at such a rate that it reacts as rapidly as added, excess propylene oxide in the reaction vessel is avoided, which results in increased control of the reaction, and an unexpectedly improved yield of less-unsaturated and relatively homogeneous high molecular weight copolymer product having a high molecular weight hydrophobic region.

The present invention includes a method of delivering therapeutic drugs to a human or animal for treating disease states such as, but not limited to, bacterial infection and infections caused by HIV and other DNA and RNA viruses. The present invention relates particularly to compositions and methods for treating infectious diseases and genetic disorders through gene therapy and intracellular delivery of antisense oligonucleotides or other nucleic acid sequences.

The present invention also comprises use of the new copolymer as a vaccine adjuvant which, when admixed with an antigen or hapten and administered into a human or animal, will induce a more intense immune response to the antigen than when the antigen is administered alone. In many cases, the adjuvant that is described as the present invention will increase overall titer of antibodies specific for the vaccine antigen and induce cellular immune responses specific for the vaccine antigen. The present invention also includes vaccines comprising an antigen or group of antigens and the new class of polyoxyethylene/polyoxypropylene copolymers which are present in the composition as an adjuvant.

Accordingly, it is an object of the present invention to provide a composition and a method for making the composition comprising a polyoxyethylene/polyoxypropylene block copolymer that has an internal polyoxypropylene block with a molecular weight of between approximately 7000 and 20,000 Daltons and the polyoxypropylene block copolymer being substantially free of unsaturation.

Another object of the present invention is to provide compounds that can stimulate the immune system and act as an effective vaccine adjuvant for use in a human or animal.

Still another object of the present invention is to provide a composition with superior adjuvant properties that facilitates vaccination with lower amounts of antigen.

Another object of the present invention is to provide compositions that facilitate delivery of one or more therapeutic nucleic acid sequence function altering agents into the interior of a cell, such as a phagocytic cell, when admixed with a therapeutic agent.

Another object of the present invention is to provide compositions that act synergistically with a delivered agent once inside a cell.

Still another object of the invention is to provide nonionic block copolymers having surfactant properties that facilitate the transmission and introduction across cellular plasma membranes of nucleic acid sequences and compounds capable of altering nucleic acid sequence function.

A further object of the present invention is to provide compositions and a method for treating genetic and physiologic disorders using nucleic acid sequences and antisense oligonucleotides in combination with nonionic block copolymers.

Another object of the present invention is to provide compositions and a method useful for manipulating the expression of genes using triplex DNA compounds.

Yet another object of the invention is to provide DNA vaccines.

Yet another object of the present invention is to provide a method for synthesizing polyoxyethylene/polyoxypropylene block copolymer where the polyoxypropylene block polymer has a molecular weight of at least 7000 Daltons and is substantially free of unsaturation.

These and other objects, features and advantages of the present invention will become apparent after a review of the following detailed description of the disclosed embodiments and the appended claims.

BRIEF DESCRIPTION OF THE FIGURES

FIG. 10 shows serum antibody responses to ovalbumin (OVA) in C57BL/6 mice following two immunizations with suboptimal doses of OVA alone or with experimental adjuvants. Six animals/group were tested using a standard ELISA and a $\log_5$ titration of sera ($1/100$–$1/25,000$). Data are shown as the mean absorbance (450 nm) for each serum dilution for individual mice.

FIG. 11 displays serum antibody responses to OVA in C57BL/6 mice following two immunizations with suboptimal doses of OVA formulated with clinically relevant adjuvants, alum, saponin (Quil-A; Superfos Biosector), Ribi adjuvant (oil-in-water (O/W) containing 4'-monophosphoryl lipid A, Ribi Immunochemical, Inc., Hamilton, Mont.), and CRL1005. Six animals/group were tested using a standard ELISA and a $\log_5$ titration of sera ($1/100$–$1/25,000$). Data are shown as the mean absorbance (450 nm) for each serum dilution for individual mice.

DETAILED DESCRIPTION OF THE INVENTION

Figure 1:
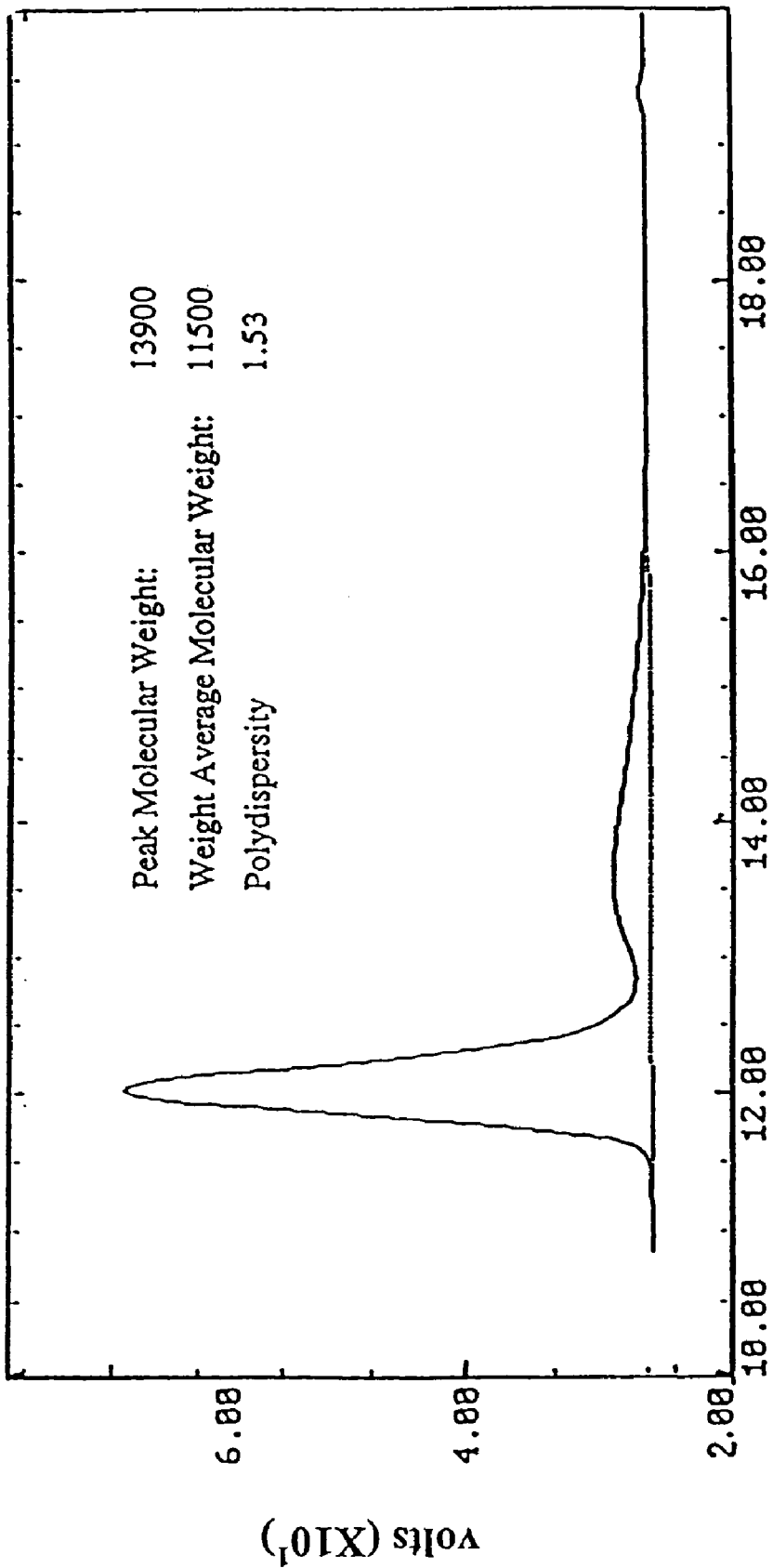
FIG. 1 is a gel permeation chromatogram of CRL1005 synthesized as described in Example I.

The term "antigen" is defined as anything that can serve as a target for an immune response. The term "adjuvant" means compounds that, when used in combination with specific vaccine immunogens in formulations, augment or otherwise alter or modify the resultant immune responses. The term "vaccine" is defined herein as a suspension or solution of antigenic moieties, usually consisting of inactivated infectious agents, or some part of the infectious agents, that is injected into the body to produce active immunity. The antigenic moiety making up the vaccine can be either a live or killed microorganism, or a natural product purified from a microorganism or other cell including, but not limited to tumor cells, a synthetic product, a genetically engineered protein, peptide, polysaccharide or similar product or an allergen. The antigenic moiety can also be a subunit of a protein, peptide, polysaccharide or similar product. The term "cell mediated immunity" is defined as an immune response mediated by cells or the products they produce, such as cytokines, rather than by antibody. It includes, but is not limited to, delayed type hypersensitivity and cytotoxic T cells. The term "adjuvant" as used herein is any substance whose admixture with an injected immunogen modifies the immune response. Modification of the immune response means augmentation, intensification, or broadening the specificity of either or both antibody and cellular immune responses. Modification of the immune response can also mean decreasing or suppressing certain antigen-specific immune responses such as the induction of tolerance. A "hapten" is defined herein as a substance that reacts selectively with appropriate antibodies or T cells but the hapten itself is usually not immunogenic. Most haptens are small molecules or small parts of large molecules, but some macromolecules can also function as haptens.

The present invention comprises a method of synthesizing high molecular weight polyoxyethylene/polyoxypropylene block copolymers. The present invention also includes high molecular weight polyoxyethylene/polyoxypropylene block copolymers. The nonionic block copolymers have the following general formula:

$$HO(C_2H_4O)_a(C_3H_6O)_b(C_2H_4O)_aH$$

wherein b represents a number such that the molecular weight of the hydrophobe ($C_3H_6O$) is between approximately 7000 and 20,000 Daltons and a represents a number such that the percentage of hydrophile ($C_2H_4O$) is between approximately 1% and 40% by weight.

According to the present invention, the nonionic block copolymers are synthesized using the following procedure. An initiator molecule such as propylene glycol, ethylene glycol or diethylene glycol, is mixed with the catalyst, cesium hydroxide, in mole ratios from approximately 2:1 to 8:1. Throughout the synthesis, all reactants and reactions are kept in an oxygen-free environment.

The catalyst and the initiator are placed in a glass-lined pressure reactor and heated. Propylene oxide gas is added to the reactor vessel by a rate limiting, vapor phase addition method. The reactants in the reactor are stirred and heated, at temperatures ranging from 90° C. to 120° C. The propylene oxide-initiator molecule reaction is allowed to continue until the product polymers are the desired molecular weight, as determined, for example, by gel permeation chromatography. The molecular weights of the hydrophobic portion of the molecule ($C_3H_6O$) can range from 7,000 to 20,000 Daltons, more particularly from 9,000 to 15,000 Daltons, and even more particularly, from 10,000 to 14,000 Daltons. The size of the hydrophobic portion of the molecule can be varied by changing the amount of propylene oxide used in the reaction. After reacting the propylene oxide required, ethylene oxide is added to the polypropylene oxide hydrophobe. The polyoxyethylene portion of the molecule is preferably between 1% and 30% of the total weight of the polymer with a more preferable range of between 3% and 25% of the total weight of the polymer.

The amount of ethylene oxide (EtO) to be used in the next part of the synthesis is determined from the amount of propylene oxide (PrO) used. For example, the amount of ethylene oxide required to produce a polymer with a total polyethyleneoxide content of 5% is calculated by the following formula:

$$\frac{\text{Wt of PrO added}}{19} = \text{grams of EtO required}$$

The grams of ethylene oxide required equals the weight of propylene oxide over 19. The ethylene oxide is then added to the reactor vessel under the same conditions as above. After the ethylene oxide is reacted, the molecular weight of the polymer is determined using gel permeation chromatography.

The product polymer is then preferably treated with magnesium silicate (Magnesol), diatomaceous earth (Celite), and water. The water, diatomaceous earth, and magnesium silicate are added in at least three aliquots to the reactor which is maintained in the oxygen-free environment, at a high heat, with stirring, over six hours. It has been found that adding these reagents in aliquots more effectively removes the residual catalyst than adding all at once. At the end of these additions, the reactor vessel is allowed to return to room temperature. Again, samples of the product polymer are taken for molecular weight determination by gel permeation chromatography. While maintaining the oxygen-free environment, the product polymer is filtered and packaged.

The high molecular weight nonionic copolymers of the present invention are useful as general surfactants and as adjuvants in vaccines. Vaccines made with the high molecular weight copolymers induce higher antibody titers in animals than do vaccines which do not contain the copolymers (see Examples III and IV below). Furthermore, use of the composition of the present invention enables effective vaccination with lower amounts of antigen in the vaccine. The antigen component of the vaccine may comprise one or several antigenic molecules such as haptens, proteins, nucleic acids, tumor cells and antigens from various sources such as infectious agents.

An effective vaccine must induce an appropriate response to the correct antigen or antigens. There are several distinct types of immune responses which vary in their ability to confer protection against particular diseases. For example, antibodies may confer protection against bacterial infections, but cell mediated immunity is required for eliminating from the body many viral infections and tumors. There are multiple distinct types of antibody and cell-mediated immune responses. Cell-mediated responses are divided into two basic groups: 1) delayed-type hypersensitivity in which T cells act as helper or suppressor cells indirectly via macrophages and other cells or cell products and via indirect interactions through products secreted from the T cells such as cytokines, and 2) cytotoxicity in which specialized T-cells specifically and directly attack and kill infected cells.

Thus, the present invention comprises an improved adjuvant. In one embodiment of the present invention, an antigen is admixed with an effective amount of an adjuvant, the adjuvant comprises a surface-active copolymer having the following general formula:

$$HO(C_2H_4O)_a(C_3H_6O)_b(C_2H_4O)_aH$$

wherein "b" represents a number such that the molecular weight of the hydrophobe ($C_3H_6O$) is between approximately 7000 and 20,000 Daltons and "a" represents a number such that the percentage of hydrophile ($C_2H_4O$) is between approximately 1% and 40% by weight.

A preferred surface-active copolymer that can be used as a vaccine adjuvant has the following formula:

$$HO(C_2H_4O)_a(C_3H_6O)_b(C_2H_4O)_aH$$

wherein "b" represents a number such that the molecular weight of the hydrophobe ($C_3H_6O$) is between approximately 9000 Daltons and 15,000 Daltons and "a" represents a number such that the percentage of hydrophile ($C_2H_4O$) is between approximately 3% and 35%.

Another preferred surface-active copolymer that can be used as a vaccine adjuvant has the following formula:

$$HO(C_2H_4O)_a(C_3H_6O)_b(C_2H_4O)_aH$$

wherein "b" represents a number such that the molecular weight of the hydrophobe ($C_3H_6O$) is approximately 9000 Daltons and "a" represents a number such that the percentage of hydrophile ($C_2H_4O$) is approximately 3%.

Another preferred surface-active copolymer that can be used as a vaccine adjuvant has the following formula:

$$HO(C_2H_4O)_a(C_3H_6O)_b(C_2H_4O)_aH$$

wherein "b" represents a number such that the molecular weight of the hydrophobe ($C_3H_6O$) is approximately 11000 Daltons and "a" represents a number such that the percentage of hydrophile ($C_2H_4O$) is approximately 5%.

Antigens that can be used in the present invention are compounds which, when introduced into a mammal, will result in the formation of antibodies and cell mediated immunity. Representative of the antigens that can be used according to the present invention include, but are not limited to, natural, recombinant or synthetic products derived from viruses, bacteria, fungi, parasites and other infectious agents in addition to autoimmune diseases, hormones or tumor antigens which might be used in prophylactic or therapeutic vaccines and allergens. The viral or bacterial products can be components which the organism produced by enzymatic cleavage or can be components of the organism that were produced by recombinant DNA techniques that are well-known to those of ordinary skill in the art. The following is a partial list of representative antigens:

Viruses
  Rotavirus
  Foot and mouth disease
  Influenza
  Parainfluenza
  Herpes species,
    Herpes simplex,
    Epstein Barr virus
    Chicken pox,
    pseudorabies
    Cytomegalovirus
  Rabies
  Polio
  Hepatitis A
  Hepatitis B
  Hepatitis C
  Hepatitis E
  Measles
  Distemper
  Venezuelan equine encephalomyelitis
  Feline leukemia virus
  Reovirus
  Respiratory sycytial virus
  Lassa fever virus
  Polyoma tumor virus
  Canine parvovirus
  Papilloma virus
  Tick borne encephalitis
  Rinderpest
  Human rhinovirus species
  Enterovirus species, Mengo virus
  Paramyxovirus
  Avian infectious bronchitis virus
  HTLV 1
  HIV-1
  HIV-2
  Influenza A and B
  LCMV (lymphocytic choriomeningitis virus)
  Parovirus
  Adenovirus
  Togavirus (rubella, yellow fever, dengue fever)
  Bovine respiratory syncicial virus
  Corona virus Bacteria
  *Bordetella pertussis*
  *Brucella abortis*
  *Escherichia coli*
  *Salmonella* species, *salmonella typhi*
  *Streptococci*
  *Vibrio* (*V. cholera, V. parahaemolyticus*)
  *Shigella*
  *Pseudomonas*
  *Brucella* species
  *Mycobacteria* species (tuberculosis, avium, BCG, leprosy,)
  *Pneumococci*
  *Staphlylococci*
  *Enterobacter* species
  *Rochalimaia henselae*
  *Pasterurella* (*P. haemolytica, P. multocida*)
  *Chlamydia* (*C. trachomatis, C. psittaci, Lymphogranuloma venereum*)
  Syphilis (*Treponema pallidum*)

*Haemophilus* species
Mycoplasmosis
Lyme disease (*Borrelia burgdorfen*)
Legionnaires' disease
Botulism (*Colstridium botulinum*)
*Corynebacterium diphtheriae*
*Yersinia entercolitica*

Ricketsial Infections
  Rocky mountain spotted fever
  Thyphus
  Ehrlichia

Parasites and Protozoa
  Malaria (*Plasmodium falciparum, P. vivax, P. malariae*)
  Schistosomes
  Trypanosomes
  Leishmania
  Filarial nematodes
  Trichomoniasis
  Sarcosporidiasis
  *Taenia* (*T. saginata, T. solium*)
  Leishmania
  *Toxoplasma gondii*
  Trichinelosis (*Trichinella spiralis*)
  Coccidiosis (*Eimeria* species)

Fungus
  *Cryptococcus neoformans*
  *Candida albicans*
  *Apergillus fumigatus*
  Coccidioidomycosis Subunit Recombinant Proteins
  Herpes simplex
  Epstein Barr virus
  Hepatitis B
  Pseudorabies
  Flavivirus, Denge, Yellow fever
  *Neisseria gonorrhoeae*
  Malaria: circumsporozoite protein, merozoite protein
  Trypanosome surface antigen protein
  Pertussis
  Alphaviruses
  Adenovirus Proteins
  Diphtheria toxoid
  Tetanus toxoid
  Meningococcal outer membrane protein (OMP)
  Streptococcal M protein
  Hepatitis B
  Influenza hemagglutinin
  Cancer antigen, tumor antigens
  Toxins, Exotoxins, Neurotoxins
  Cytokines and Cytokine receptors
  Monokines and monokine receptors Synthetic Peptide
  Malaria
  Influenza
  Foot and mouth disease virus
  Hepatitis B. Hepatitis C Polysaccharide
  Pneumococcal polysaccharide
  *Haemophilis influenza* polyribosyl-ribitolphosphate (PRP)
  *Neisseria meningitides*
  *Pseudomonas aeruginosa*
  *Klebsiella pneumoniae*

Oligosaccharide
  Pneumococcal

Allergens
  Plant pollens
  Animal dander
  dust mites

Haptens are compounds which, when bound to an immunogenic carrier and introduced into a chordate, will elicit formation of antibodies specific for the hapten. Representative of the haptens are steroids such as estrogens and cortisones, low molecular weight peptides, other low molecular weight biological compounds, drugs such as antibiotics and chemotherapeutic compounds, industrial pollutants, flavoring agents, food additives, and food contaminants, and/or their metabolites or derivatives.

When used as an adjuvant, the polyoxyethylene/polyoxypropylene block copolymer of the present invention can be administered to a human or animal by a variety of routes including, but not limited to, intramuscular injection, intravenous injection, intraperitoneal injection, orally, rectal, vaginal, sublingually, and nasally.

The present invention also comprises a therapeutic delivery composition effective for treating a disease state comprising an administerable admixture of an effective amount of a therapeutic compound capable of altering nucleic acid sequence function and an effective amount of a surface active nonionic block copolymer having the following general formula:

$$HO(C_2H_4O)_a(C_3H_6O)_b(C_2H_4O)_aH$$

wherein "b" represents a number such that the molecular weight of the hydrophobe ($C_3H_6O$) is between approximately 7000 and 20,000 Daltons and "a" represents a number such that the percentage of hydrophile ($C_2H_4O$) is between approximately 2% and 40% by weight.

Another preferred surface-active copolymer that can be used as a therapeutic delivery agent has the following formula:

$$HO(C_2H_4O)_a(C_3H_6O)_b(C_2H_4O)_aH$$

wherein "b" represents a number such that the molecular weight of the hydrophobe ($C_3H_6O$) is approximately 13000 Daltons and "a" represents a number such that the percentage of hydrophile ($C_2H_4O$) is approximately 5%.

Another preferred surface-active copolymer that can be used as a therapeutic delivery agent has the following formula:

$$HO(C_2H_4O)_a(C_3H_6O)_b(C_2H_4O)_aH$$

wherein "b" represents a number such that the molecular weight of the hydrophobe ($C_3H_6O$) is approximately 11000 Daltons and "a" represents a number such that the percentage of hydrophile ($C_2H_4O$) is approximately 15%.

A particularly useful composition is an admixture of a compound capable of altering gene expression and/or protein translation, such as an antisense oligonucleotide, a triplex DNA compound, a ribozyme or other compound capable of altering nucleic acid sequence function, and the above-described nonionic block copolymer.

The composition of the present invention can be administered by a number of routes including, but not limited to topical, transdermal, oral, trans-mucosal, subcutaneous injection, intravenous injection, intraperitoneal injection and intramuscular injection.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Synthesis of CRL1005

The poloxamer, CRL1005, is a tri-block copolymer of polyoxyethylene (POE) and polyoxypropylene (POP) with the middle POP hydrophobe having an average molecular weight of approximately 12000 Daltons, and the polymer having 5% POE. The initiator for the synthesis is propylene glycol. The catalyst is cesium hydroxide ($CsOH \cdot H_2O$) in a mole ratio of 2:1 (initiator:catalyst).

About 3.52 gm of cesium hydroxide was dispensed and then transferred into a glass-lined pressure reactor. The reactor was heated under vacuum at temperature of 100° C. for approximately 20 hours to dry the CsOH. After the reactor has cooled to a temperature below 50° C., an amount of 3.18 gm of the initiator, propylene glycol, was weighed and charged into the reactor.

A reservoir containing propylene oxide (PrO) was connected to the reactor. The reservoir was maintained at 30° C. in a silicone oil heat bath. Only the propylene oxide vapors from the reservoir were allowed to react with the propylene glycol initiator in the reactor. The reactor was heated and maintained at 100° C. while stirring throughout the propylene oxide addition procedure. The PrO addition reaction was continued until a total of 1073.72 gm of PrO was added to the reactor.

Samples were taken for analysis for molecular weight determination, using polyethylene glycol (PEG) standards to establish the calibration curve.

56.85 gm of ethylene oxide was charged to the reactor under the same condition as the PrO, except the ethylene oxide glass reservoir was kept at room temperature Ethylene oxide in the reactor was allowed to continue to react to completion. At this point, more samples were taken for gel permeation chromatography (GPC) analysis.

The polymer was treated with magnesium silicate (Magnesol) (approximately 4×wt. of $CsOH \cdot H_2O$), diatomaceous earth (Celite) (approximately 0.3×wt of Magnesol), and water (approximately 0.11×wt. of $CsOH \cdot H_2O$). An amount of 0.37 gm of water was dispensed and stirred into the reactor under a slight purge of nitrogen. A mixture of 14.15 gm of Magnesol and 4.32 gm of Celite was separated into three nominally equal portions. Each portion of the mixture was added, in three 2 hour intervals, to the reactor while heating at 110° C. and stirring at approximately 60 rpm under a slight nitrogen purge. Adding the mixture in several portions is important to effectively remove the residual catalyst. At the end of the 6 hour treatment period, the reactor was allowed to cool to room temperature before in-process samples were taken for GPC analysis.

The treated polymer was filtered The polymer and filter funnel were heated to 70° C. Nitrogen was applied through a pressure holder to approximately 40 psig to facilitate the filtration process. The polymer was collected in glass Quorpak bottles for storage under nitrogen and refrigeration.

EXAMPLE II

Physical Properties of the CRL1005

The CRL1005 synthesized in Example I was analyzed using gel permeation chromatography and nuclear magnetic resonance. The results of the analysis are as follows:

| GPC ANALYSIS | |
|---|---|
| Peak Mwt | 13763 |
| Wt. Av Mwt | 11621 |
| % of Low Mwt | 20.64 |
| where Mwt is molecular weight | |
| Unsaturation, meq/gm | 0.0561 |
| Percent EO, by NMR | 5.70 |

The fractions were characterized by gel permeation chromatography using polyethylene glycol (PEG) standards, NMR, and unsaturation. Gel permeation chromatography provided different average molecular weights. Percentage of ethylene oxide units was determined from NMR. Unsaturation was measured by wet chemistry and provided amount of —CH=CH— groups present in the end groups. FIG. 1 shows a gel permeation chromatogram of CRL1005.

EXAMPLE III

Particle Formation by Block Copolymers

Figure 2A:
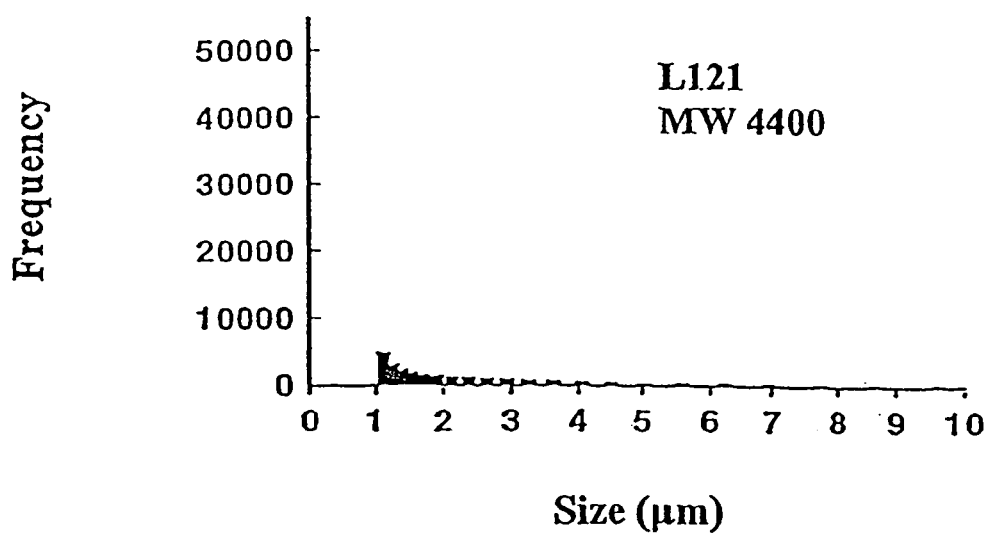
FIG. 2 shows particle size distribution of 2.5% L121 (top) and 2.5% CRL1005 copolymers in phosphate buffered saline. Analysis was done using a Model 770 AccuSizer and test preparations of identical volume. Data are shown as frequency (total numbers)/size in μm.
Figure 2B:
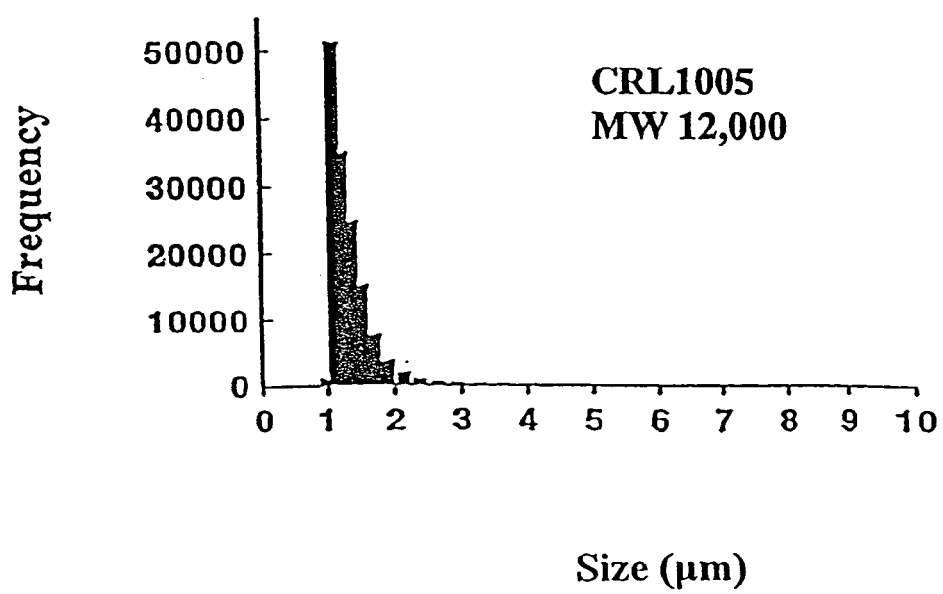

The nonionic block copolymers that have been previously evaluated as vaccine adjuvants, such as L121 and L141, are not soluble in aqueous buffers When mixed in aqueous solutions the individual polymer molecules bind to each other to form strands and ultimately an unorganized matrix or gel-like material is formed. As such, these copolymers have been used exclusively in emulsions where copolymer molecules bind to the oil/water interface. The copolymers with the large hydrophobic POP components, such as CRL1005, form small uniformed sized (1–2 µm) particles in aqueous buffers (FIG. 2).

Figure 3A:
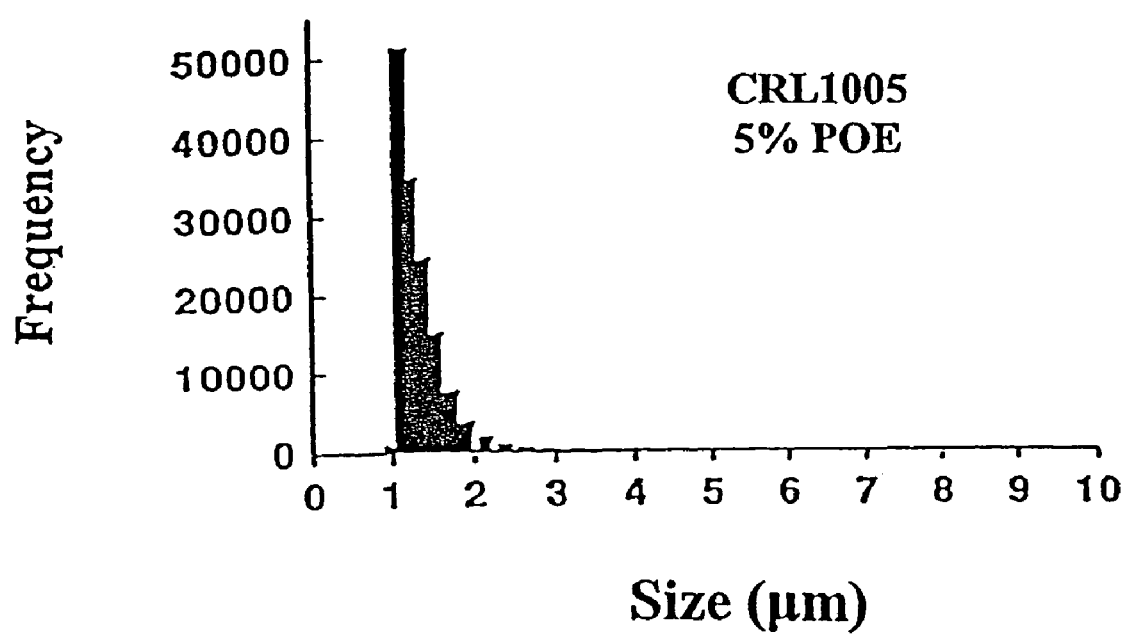
FIG. 3 shows particle size distribution of 2.5% CRL1005 (top), 2.5% CRL1011 (middle) and 2.5% CRL1053 copolymers in phosphate buffered saline. Analysis was done using a Model 770 AccuSizer and test preparations of identical volume. Data are shown as frequency (total numbers)/size in μm.
Figure 3B:
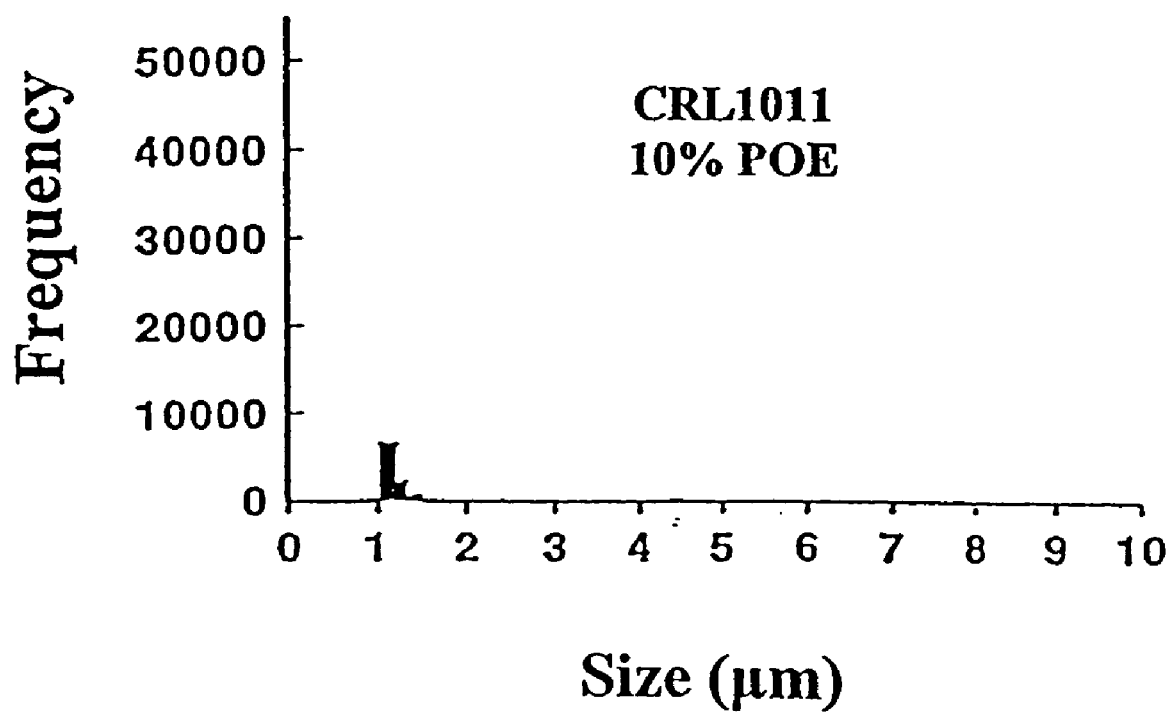
Figure 3C:
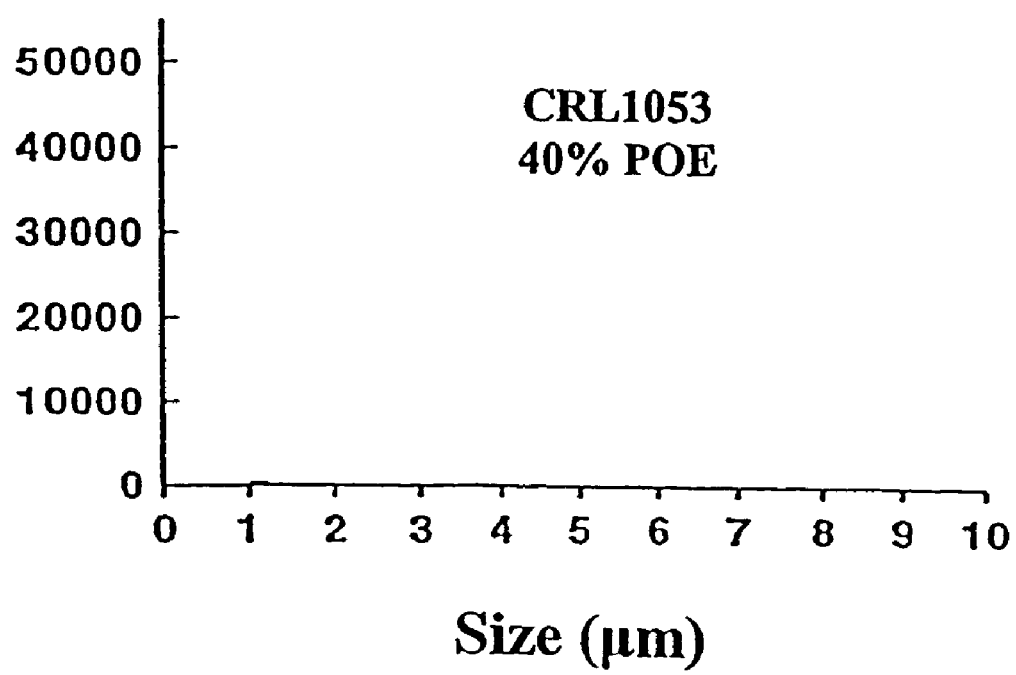

The amount of the hydrophilic POE component also effects the formation of particles in this size range. Increasing the POE content from 5% to 10% reduces the number of particles formed by 90% and higher amounts of POE essentially eliminate particle formation. In the example shown, the CRL1005 with a molecular weight of 12,000 and 5% POE forms 1–2 µm particles whereas the CRL1011 with a molecular weight of 11,200 and 10% POE is 90% less efficient at forming particles (FIG. 3). The CRL1053 with a molecular weight of 13,200 and 40% POE cannot form 1–2 µm particles.

Particulate vaccine antigens are generally more immunogenic when injected into animals than are soluble antigens. These properties have been demonstrated using several types of particulate vaccine adjuvant/delivery systems, including liposomes and poly-lactide particles. The properties of these systems that support their use in Vaccines include (1) production using biodegradable or otherwise nontoxic materials, (2) ability to produce small particles, 1–10 µm range, and (3) the ability to encapsulate or bind to vaccine antigens These are properties that are shared by the large, adjuvant active copolymers, such as CRL1005.

Particulate vaccine antigens can also be delivered orally. Particulate antigens are more effectively 'taken-up' by Peyer's patches and therefore are more efficient at inducing mucosal immune responses. The particulate property in itself appears to increase the ability of the immunogen to gain access to the Peyer's patches with the optimum size range being 1–10 μm Again, these are properties that are shared by the large, adjuvant active copolymers.

EXAMPLE IV

The effect of the CRL1005 from Example II in modulating the serological responses to a commercial influenza vaccine was examined in Balb/c mice. The commercial vaccine employed was obtained from Parke-Davis (FLUOGEN®) and was the vaccine available during the 1993 influenza season. The commercial vaccine consists of hemagglutinin (HA) and other viral components from A/TEXAS/36/91 (H1N1), A/BEIJING/32/92 (H3N2), and B/PANAMA/45/90 and contains 15 μg of each HA antigen. For experimental evaluation, the commercial vaccine was mixed in equal proportions with either buffer (0.9% NaCl;) or of copolymer (5% CRL1005, 0.9% NaCl). Mice were injected with 100 μl of the two vaccines. Serum samples were obtained prior to injection, on day 14, day 28, and day 70.

Two serological assays were employed to measure anti-influenza specific antibodies in the sera of individual immunized mice. One is an enzyme-linked immunosorbent assay (ELISA) and the other an assay to measure the ability of antibodies in serum to inhibit the influenza virus hemagglutinin-dependent agglutination of red blood cells. In the case of the latter assay, the levels of antibodies are directly correlated with the ability to neutralize virus, whereas the ELISA assay detects antibodies which may or may not be functional. Thus, the two assays independently measure serological responsiveness to the hemagglutinin (HA).

Hemagglutination Inhibition

Figure 4:
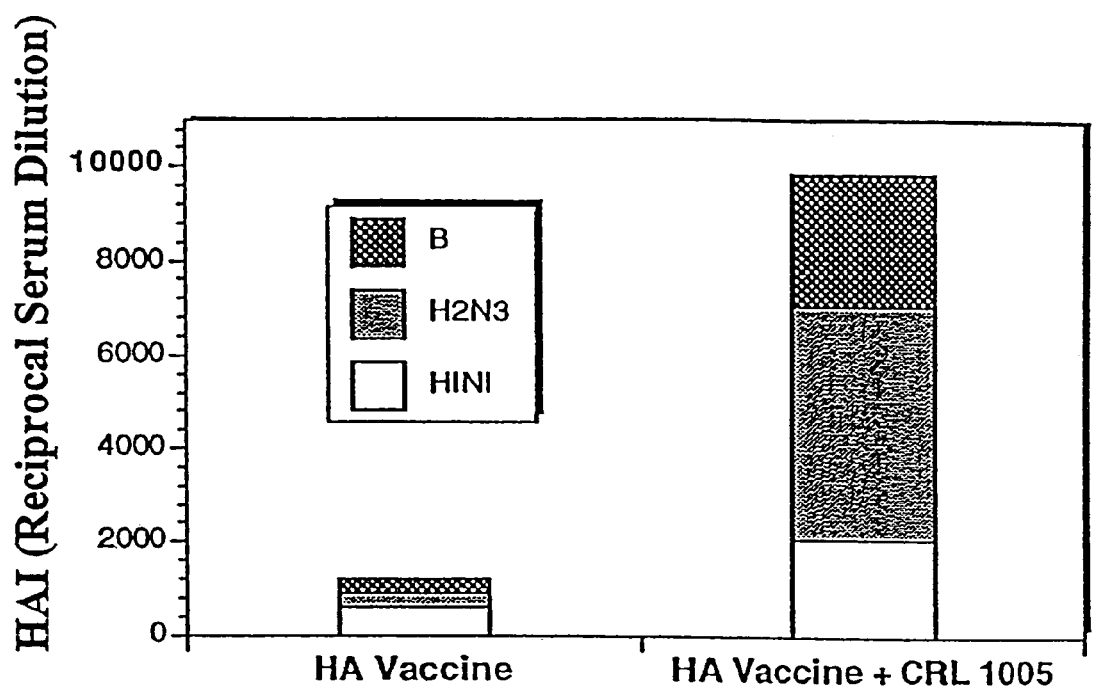
FIG. 4 is a graph showing the effect of the CRL1005 from Example II in modulating the antibody responses to a commercial influenza vaccine (FLUOGEN) in BALB/c mice as measured by the ability of antibodies in serum to inhibit the influenza virus hemagglutinin-dependent agglutination of red blood cells.

Functional antibody capable of neutralizing the influenza hemagglutinin was assayed by hemagglutination inhibition (HAI), essentially as described by the CDC Manual (Concepts and Procedures for Laboratory Based Influenza Surveillance, 1982. U.S. Department of Health and Human Services/Public Health Service/Centers for Disease Control). Serial dilutions of test sera were examined for their ability to neutralize the hemagglutinating activity of 8 units of purified hemagglutinin on chicken red blood cells. Purified hemagglutinins from the following 3 strains were used: A/YAMAGATA/32/89 (HINI), A/KISHU/54/89 (H3N2), B/AICHI/54/89. Titers are expressed as the highest serum dilution giving complete neutralization of the hemagglutinin. (FIG. 4)

EXAMPLE V

Dose Escalation and Kinetic Studies of Copolymer Adjuvant CRL1005 in a Commercial Influenza Virus Vaccine The effects of supplementing the Parke-Davis influenza virus vaccine (FLUOGEN) with copolymer adjuvant CRL1005 were investigated. The antibody titers and kinetics of antibody responses were examined as the endpoints.

A. Experimental Design

The design and results of three separate experiments are presented.

Experiment 1: Dose titration studies of the influenza virus vaccine were done to identify doses that induced measurable antibody responses after a single immunization in BALB/c mice. Antibody responses were followed for 60 days and dose levels that were optimally and suboptimally immunogenic were identified.

Experiment 2: Vaccine formulations containing these dose levels and supplemented with increasing amounts of adjuvant-active CRL1005 polymer were evaluated. Again, antibody responses were followed for 60 days and adjuvant-active doses of CRL1005 adjuvant were identified.

Experiment 3: Kinetics and duration of antibody responses were evaluated by extension of the observation and antibody testing period to 6 months.

Parke-Davis FLUOGEN influenza virus vaccine, from the 1993–1994 season, was used as both the vaccine and as the source of viral proteins for measuring antibodies. BALB/c mice were used, five per group, in groups organized based on vaccine formulations. The adjuvant is a nonionic block polymer designated CRL1005. An aqueous formulation was used for these studies. This formulation consisted of the appropriate concentration of CRL1005 polymer and FLUOGEN® mixed in saline. Under the formulation conditions used, the polymer forms 1–2 μm particles with the immunogen. The aqueous formulations were used without additional preparation. Vaccine formulations were administered by subcutaneous needle injection, total volume of 100 μl.

Ninety mice (C57BL/6) were divided into 9 test and control groups of 10 mice per group. The mice were immunized twice with 28 days between immunizations. Vaccines were administered by needle injection subcutaneously (s.c.) in a total volume of 200 μl/dose. The groups of mice were immunized according to the following format: Group 1—vehicle control (phosphate buffered saline-PBS); Group 2—15 μg of the OVA in PBS; Group 3—15 μg of the OVA adsorbed to 125 μg of alum; Group 4—15 μg of the OVA formulated with CFA in a water-in-oil (W/O) emulsion, second immunization was given with IFA; Group 5—15 μg of the OVA formulated with 20 μg Quil-A; Group 6—15 μg of OVA formulated in a W/O emulsion containing CRL1005, 2.5% concentration of 5 mg/200 μl dose; Group 7—15 μg of OVA formulated with Ribi adjuvant as an oil-in water (O/W) emulsion; Group 8—15 μg of the OVA formulated with CRL1005, 2.5% final concentration or 5 mg/200 μl dose; Group 9—15 μg of the OVA formulated with CRL1005, 5.0% final concentration or 10 mg/200 μl dose.

B. Measurement of Vaccine-induced Antibody Responses

Blood was collected via the retro-orbital sinus at various time-points, usually at 2 and 4 week intervals. Antibody levels were determined using a standard ELISA and the FLUOGEN vaccine as the source of viral proteins. A standard positive control antiserum was prepared in BALB/c mice using the FLUOGEN vaccine formulated with emulsion-based adjuvant, to induce very high-titered antibody responses in the serum. This antiserum was used to validate the ELISA and to establish a standard curve to permit direct comparison of data obtained from experiments performed at different times. This antiserum was defined arbitrarily as containing 10,000 antibody binding Units and was used as the standard to determine antibody Units for all samples obtained from experimentally vaccinated mice.

C. Results

1. Identification of Immunogenic Doses of FLUOGEN

Figure 5A:
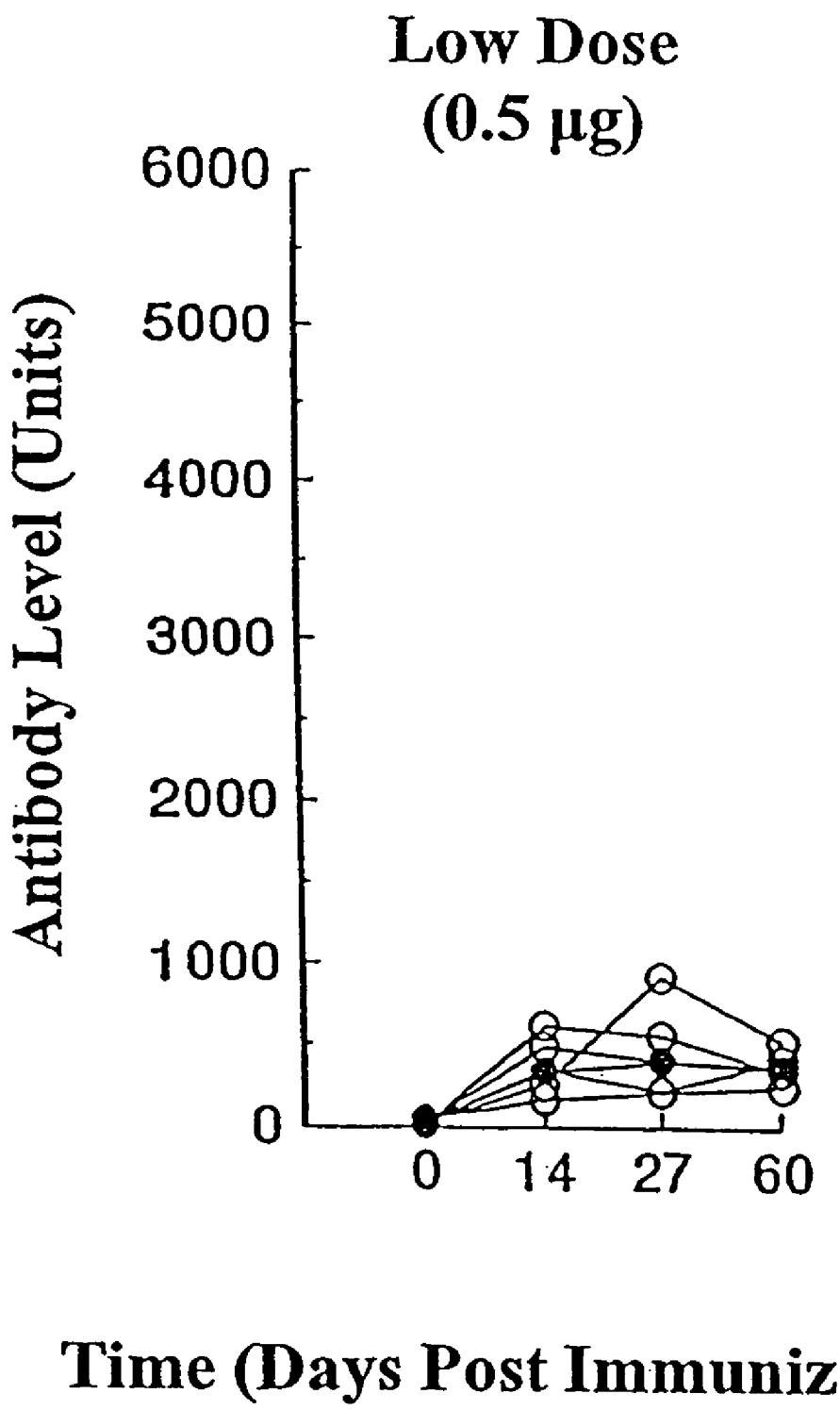
FIG. 5 displays a dose titration of FLUOGEN administered without additional adjuvants. Five mice per group were immunized once with 0.5, 1.5 or 4.5 μg of FLUOGEN and antibody responses examined over 60 days. Responses of individual mice are shown as the open circles and the geometric mean for the group is shown as the solid circles. All data are shown as antibody units.
Figure 5B:
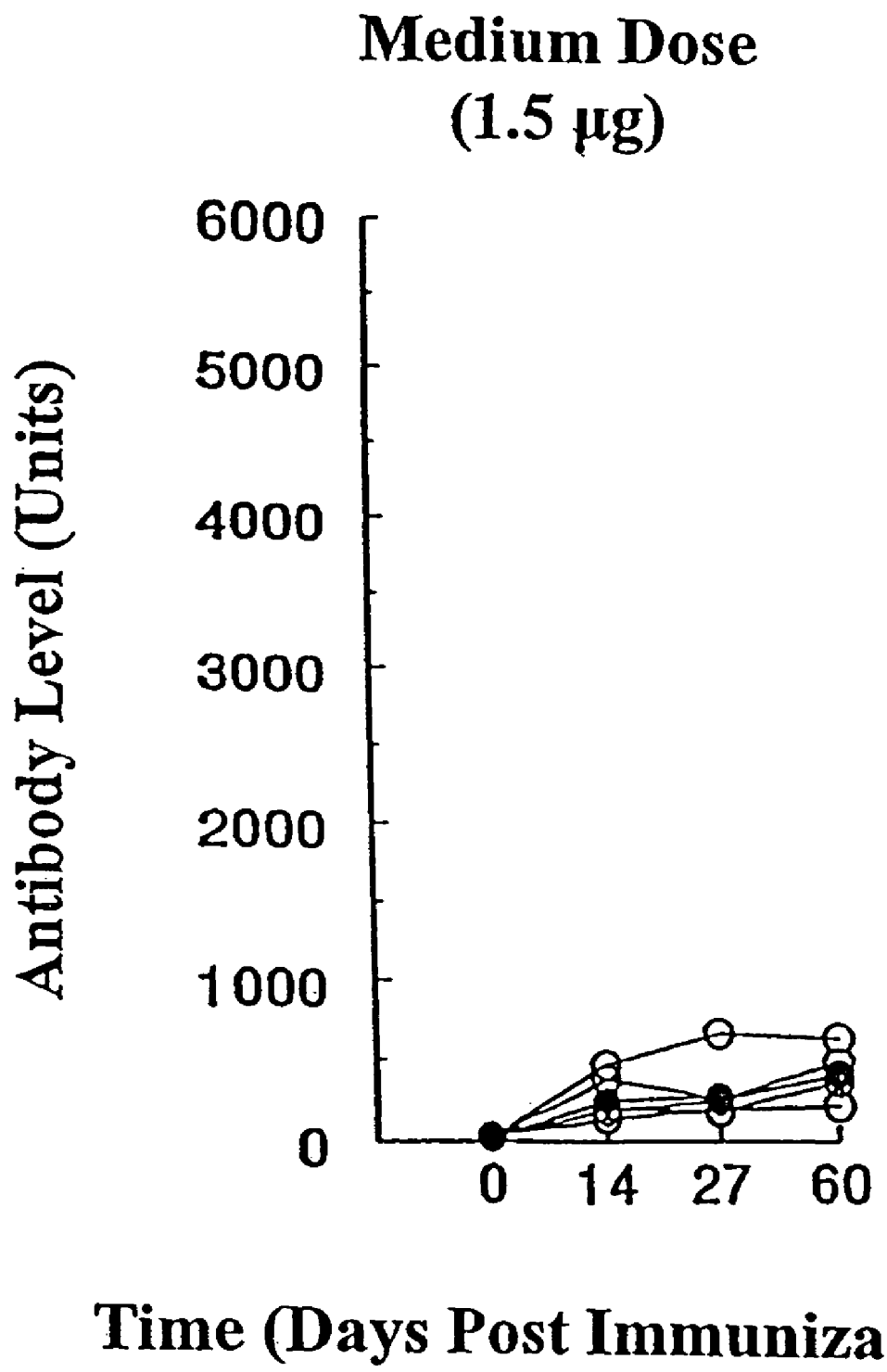
Figure 5C:
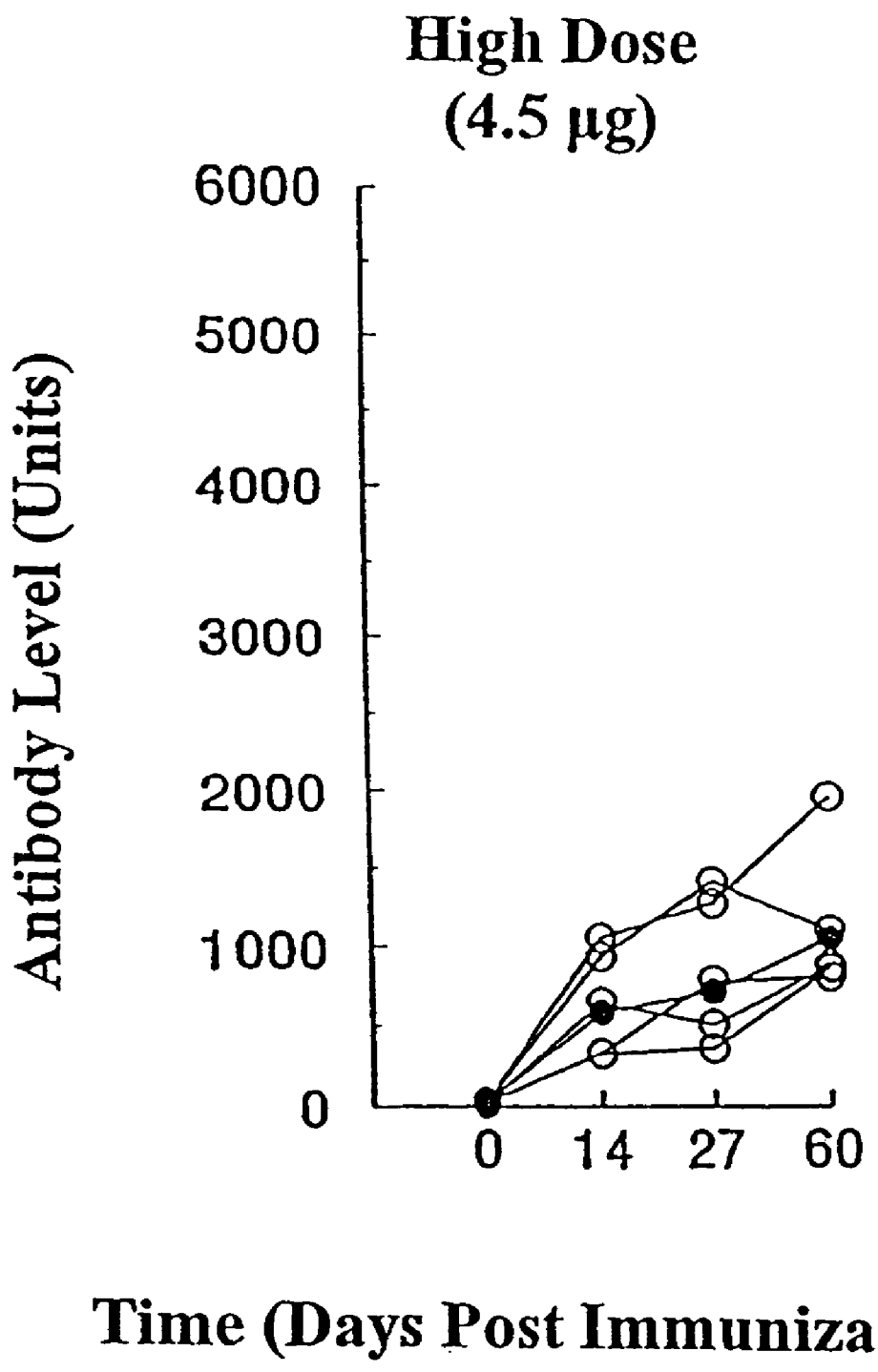

Antibody responses induced following a single immunization with 4.5, 1.5 or 0.5 μg of FLUOGEN are shown in FIG. 5. All doses were immunogenic but the 4.5 μg dose induced significantly higher antibody responses than the 1.5 and 0.5 μg doses and it was selected as the optimal dose level. Since the responses induced by the two lower concentrations were not significantly different, the 1.5 μg dose was selected as the suboptimal dose level for further studies.

2. Effect of Optivax Adjuvant on Antibody Levels, Kinetics and Duration

Figures 6A, 6B, 6C:
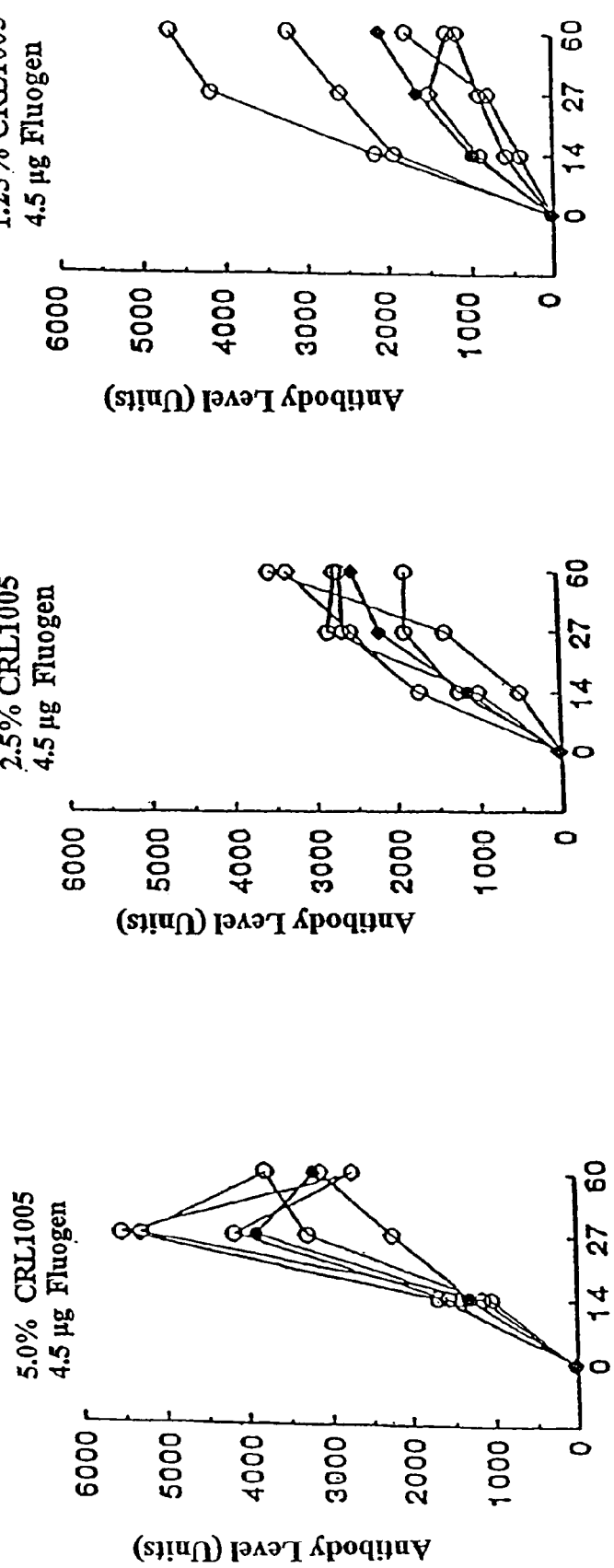
FIG. 6 shows dose titration of CRL1005 adjuvant administered with two dose levels of FLUOGEN. Five mice per group were immunized once with 4.5 μg (upper graphs) or 1.5 μg (lower graphs) of FLUOGEN formulated with 5.0, 2.5 and 1.25% CRL1005 adjuvant. Antibody responses were followed for 60 days. Responses of individual mice are shown as the open circles and the geometric mean for the group is shown as the solid circles. All data are shown as antibody units.
Figures 6D, 6E, 6F:
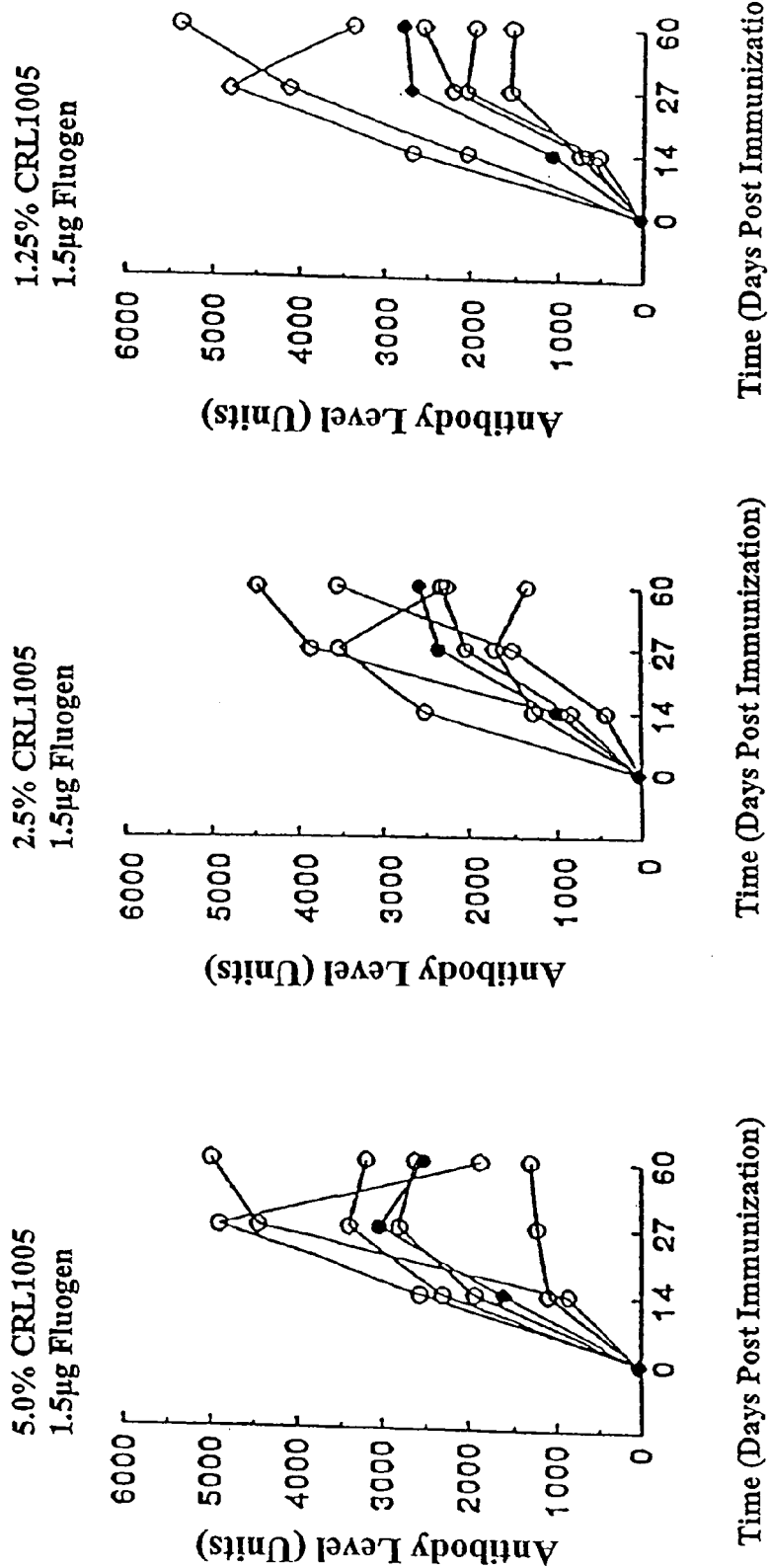
Figure 7B:
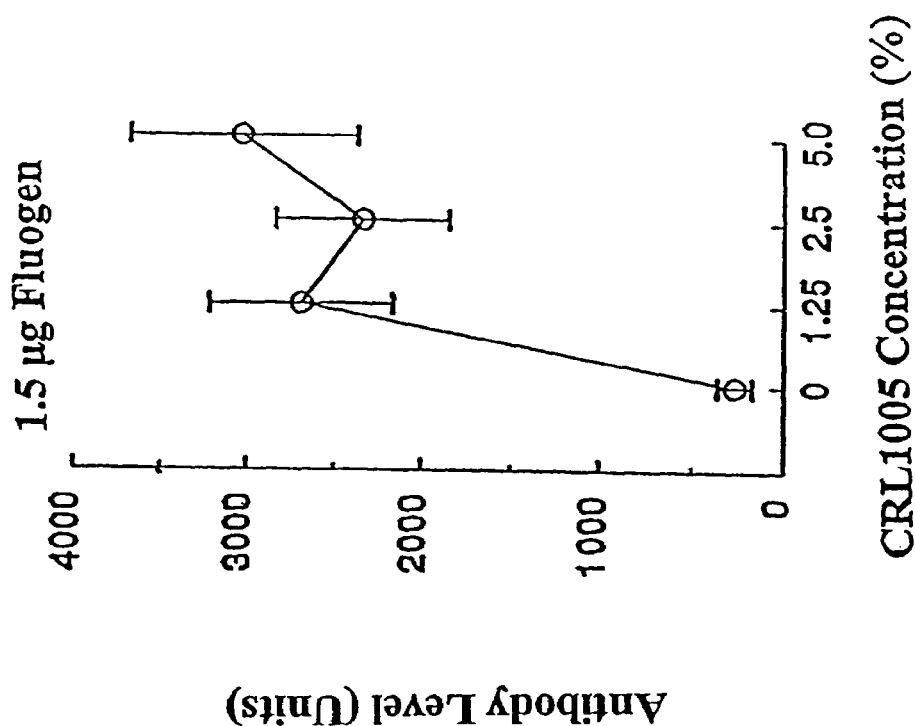
FIG. 7 demonstrates a summary and comparison of CRL1005 dose titration data using two dose levels of FLUOGEN. Five mice per group were immunized once with 4.5 or 1.5 μg of FLUOGEN formulated with 1.25, 2.5 and 5.0% CRL1005 adjuvant or without an adjuvant (0%). Antibody levels in sera of immunized mice on day 27 are shown. Data represent the geometric mean Ö 1 standard deviation for the group. All data are shown as antibody units.
Figure 7A:
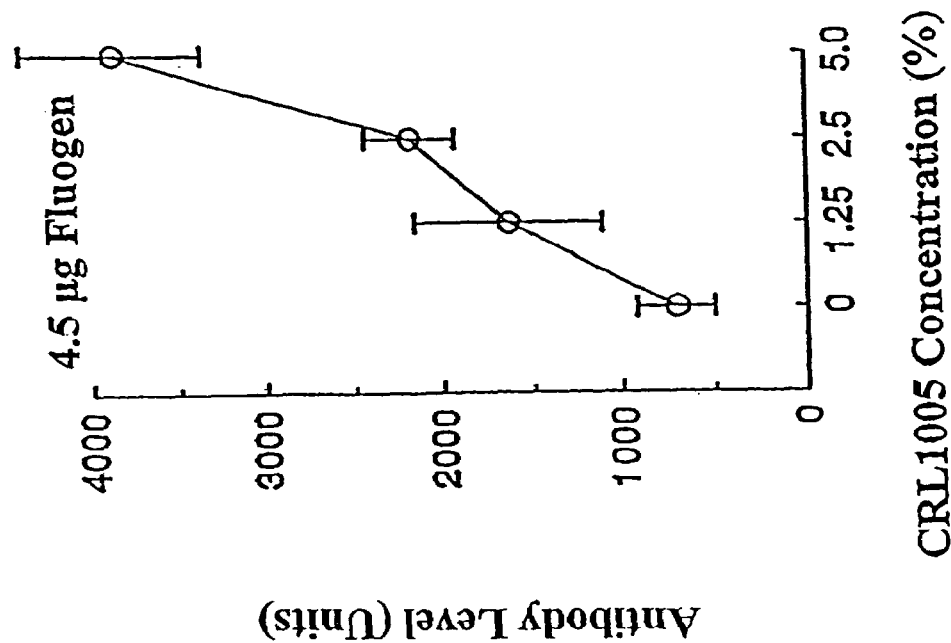

The adjuvant effects of three different concentrations, 5.0, 2.5 and 1.25%, of the CRL1005 polymer are shown in FIG. 6. All concentrations were active as adjuvants. Increases in antibody titers induced using the 4.5 µg dose of FLUOGEN ranged from 2–8 fold, with the greatest increases seen on day 27. The highest concentration of CRL1005, 5.0%, resulted in the greatest augmentation of the antibody responses for the 4.5 µg dose of FLUOGEN. Augmentation of antibody responses was more pronounced using the 1.5 µg dose of FLUOGEN. In these animals, CRL1005 increased antibody levels more than 10 fold and again the most significant differences were observed on day 27. Antibody levels were increased to levels that were not significantly different from those obtained using the higher dose of FLUOGEN (FIG. 7). These data suggest that the CRL1005 polymer adjuvant may facilitate the use of lower levels of viral proteins in vaccines.

Figures 8A, 8B:
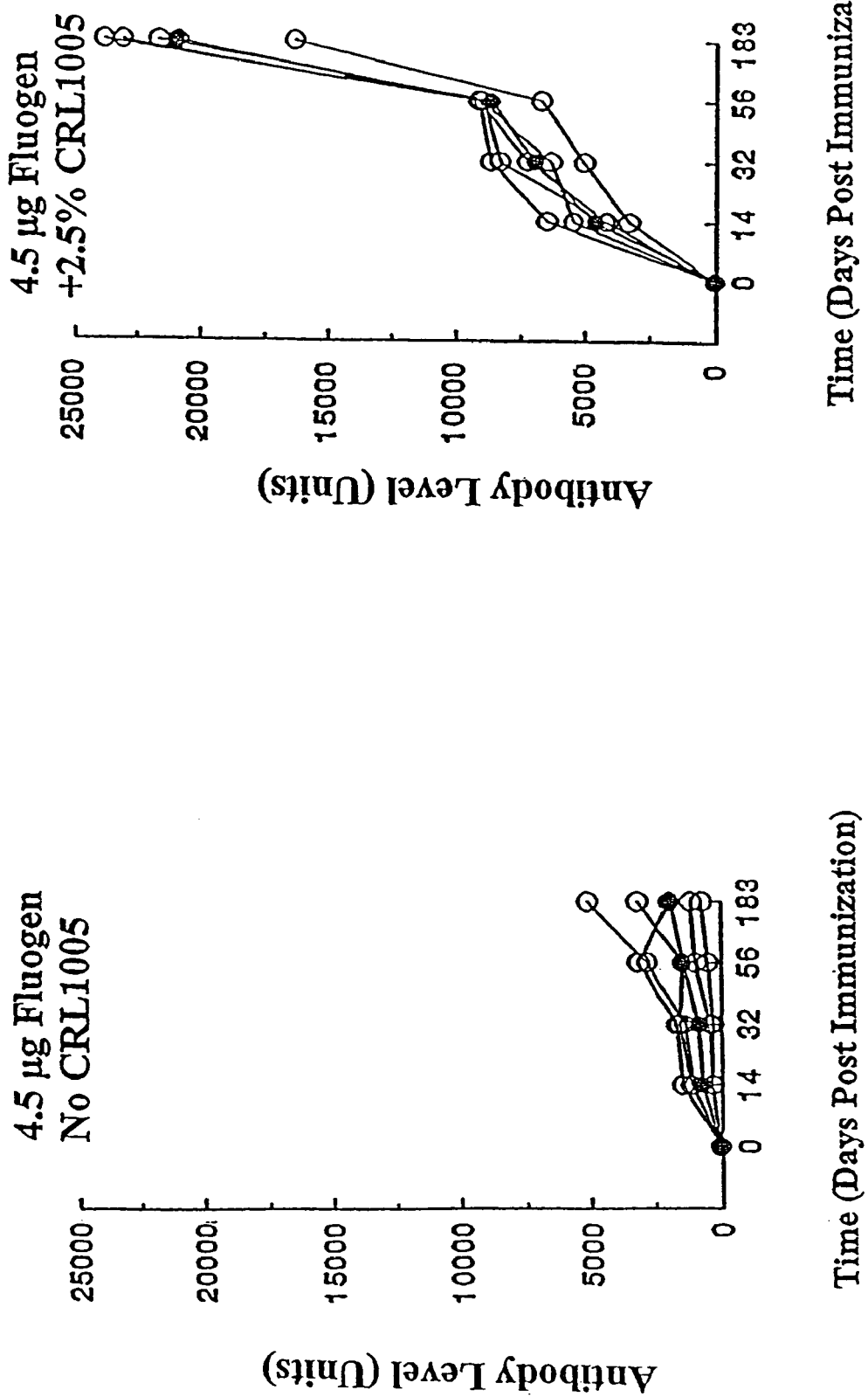
FIG. 8 shows kinetics and duration of antibody responses induced by vaccination with FLUOGEN alone or formulated with CRL1005 adjuvant. Five mice per group were immunized once with 4.5 μg of FLUOGEN formulated with 2.5% CRL1005 adjuvant. Antibody responses were followed for 6 months. Responses of individual mice are shown as the open circles and the geometric mean for the group is shown as the solid. circles. All data are shown as antibody units.

The kinetics of the primary antibody responses were shown in FIGS. 5 and 6, but these data were obtained through a period of 60 days. To evaluate the effect of CRL1005 polymer adjuvant on antibody duration, mice were immunized a single time with either 4.5 µg of FLUOGEN alone or with the same formulation supplemented with 2.5% CRL1005 and antibodies were measured within the first 60 days and again at 6 months. The results are shown in FIG. 8. Antibody levels continued to increase throughout the 6 month study period. These data indicate that the CRL1005 polymer adjuvant may prove useful for inducing long-term protection using only a limited number of vaccinations, preferably a single vaccination.

The potential value of adjuvants as components in influenza vaccines has therapeutically and biologically significant implications particularly for augmentation of immune responses in the elderly. This study demonstrated the potential utility of the CRL1005 polymer adjuvant as a component of an experimental influenza virus vaccine based on the commercial FLUOGEN vaccine. The results showed the adjuvant activity of the CRL1005 polymer adjuvant in a simple aqueous formulation with FLUOGEN. Adjuvant formulations induced higher antibody titers which continued to increase with time. The CRL1005 polymer adjuvant augmented antibody responses to suboptimal dose levels of the FLUOGEN to an even greater extent. The antibody titers reached levels similar to those induced using the higher FLUOGEN dose suggesting that lower. amounts of vaccine immunogen may be used in adjuvanted formulations. Thus, the addition of CRL1005 adjuvant to vaccine formulations may increase immunogenicity and allow for reduction in the amounts of protein immunogen(s) that are required.

EXAMPLE VI

Improved Activity of Vaccines

The influence of formulations containing the CRL1005 of Example II on the antibody response to hepatitis B surface antigen was compared with a vaccine containing aluminum hydroxide, a vaccine containing CRL1005 and aluminum hydroxide, and a vaccine containing no additions. The vaccines were made by admixing a recombinant hepatitis B surface antigen (HBsAg) with each of the additional vaccine components so that the final HBsAg concentration in each vaccine was 5 µg/ml and:
a. 2.5% CRL1005, 0.9% NaCl
b. 0.25 mg/ml Al(OH)3, 0.9% NaCl
c. 0.9% NaCl Groups of 6 or 8 BALBKc mice each received a single 100 µl dose of the above vaccines subcutaneously, so that each animal was injected with 0.5 µg of HBsAg. Serum samples were obtained from each individual animal prior to vaccination, on day 15 and on day 28.

Murine antibody concentrations against HBsAg were measured with the commercially available AUSAB® EIA (Abbott Laboratories, Abbott Park, Ill.) which uses the bridging principle to detect antibody. Specific antibody in the sample initially binds with one binding site to HBsAg immobilized on a polystyrene bead and secondarily binds to Biotin conjugated HBsAg with the other to create an antigen-antibody sandwich. The assay is therefore not species specific and can be utilized to measure murine as well as human anti-HBsAg. Murine antibody was assayed at a 1:10 dilution or higher and quantitated against a human serum standard curve. Data were expressed as mili international units (mIU) per ml, calculated by multiplying the assay value by a factor of 10.

Figure 9:
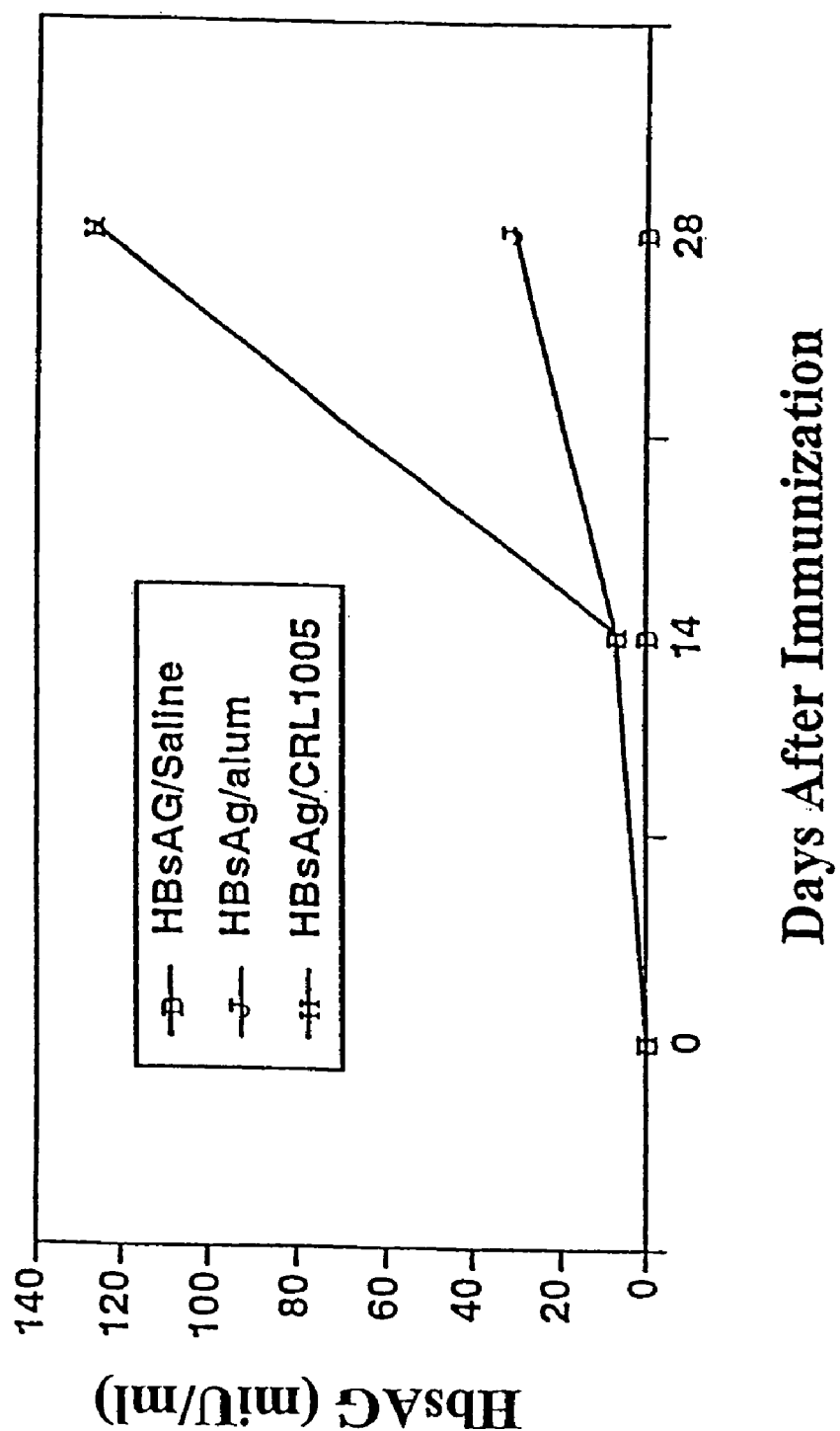
FIG. 9 is a graph showing the effect of CRL1005 on the antibody response to hepatitis B surface antigen.
Figures 12A, 12B:
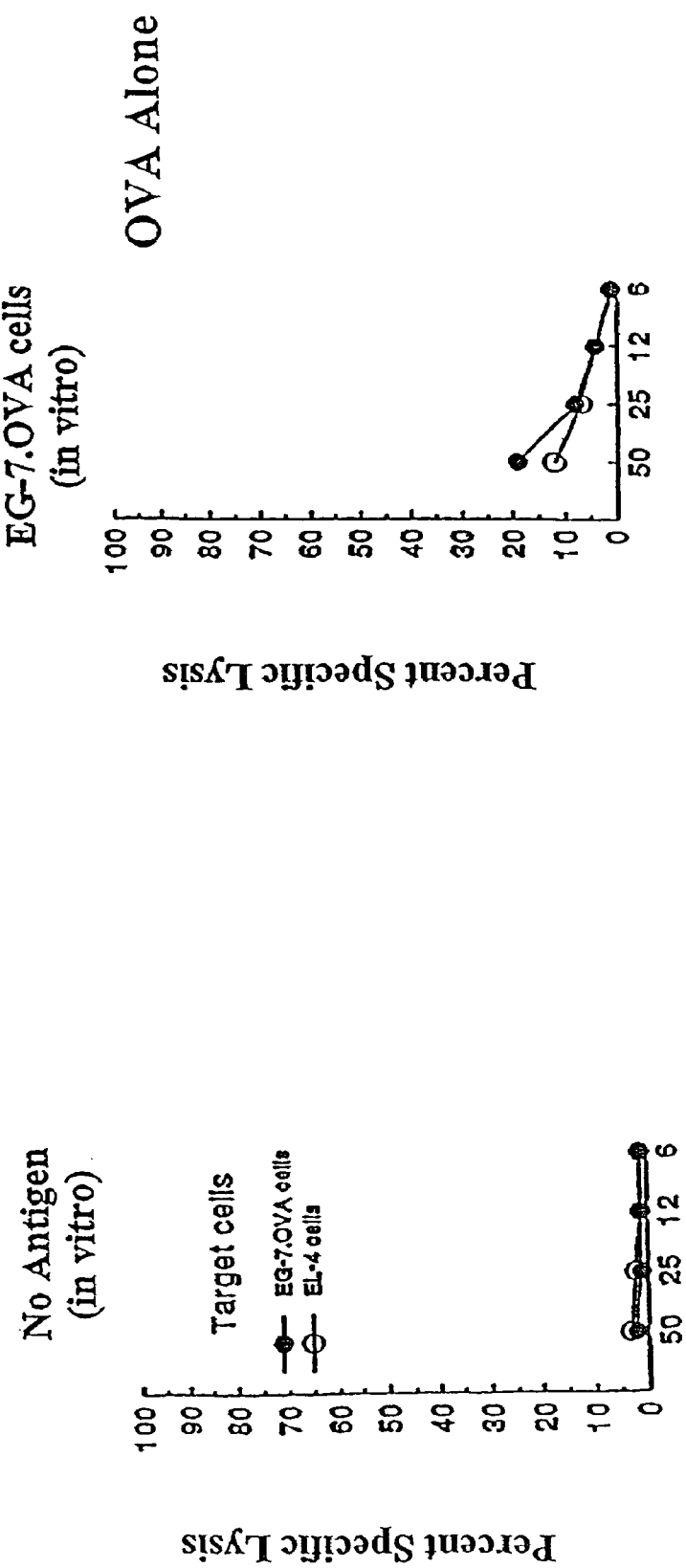
FIG. 12 presents OVA-specific cytotoxic T-lymphocyte (CTL) responses induced in C57BL/6 mice following two immunizations (days 0 and 28) with OVA in saline (left) or formulated in aqueous solution with CRL1005 copolymer adjuvant (right). A standard $^{51}$ chromium (CR)-release CTL assay was used with OVA-transfected EG-7.OVA cells and control EL-4 cells as the targets. Spleen cells were used as the source of precursor CTL, which were induced to mature to functional CTL effector cells, by culture for 6 days with irradiated EG-7.OVA or EL-4 cells. All testing was done in triplicate using a titration of Effector: Target cells, shown as ratios. Data are shown as the Percent Specific Release (Test Release–Spontaneous Release/Maximum Release–Spontaneous Release)×100.
Figures 12C, 12D:
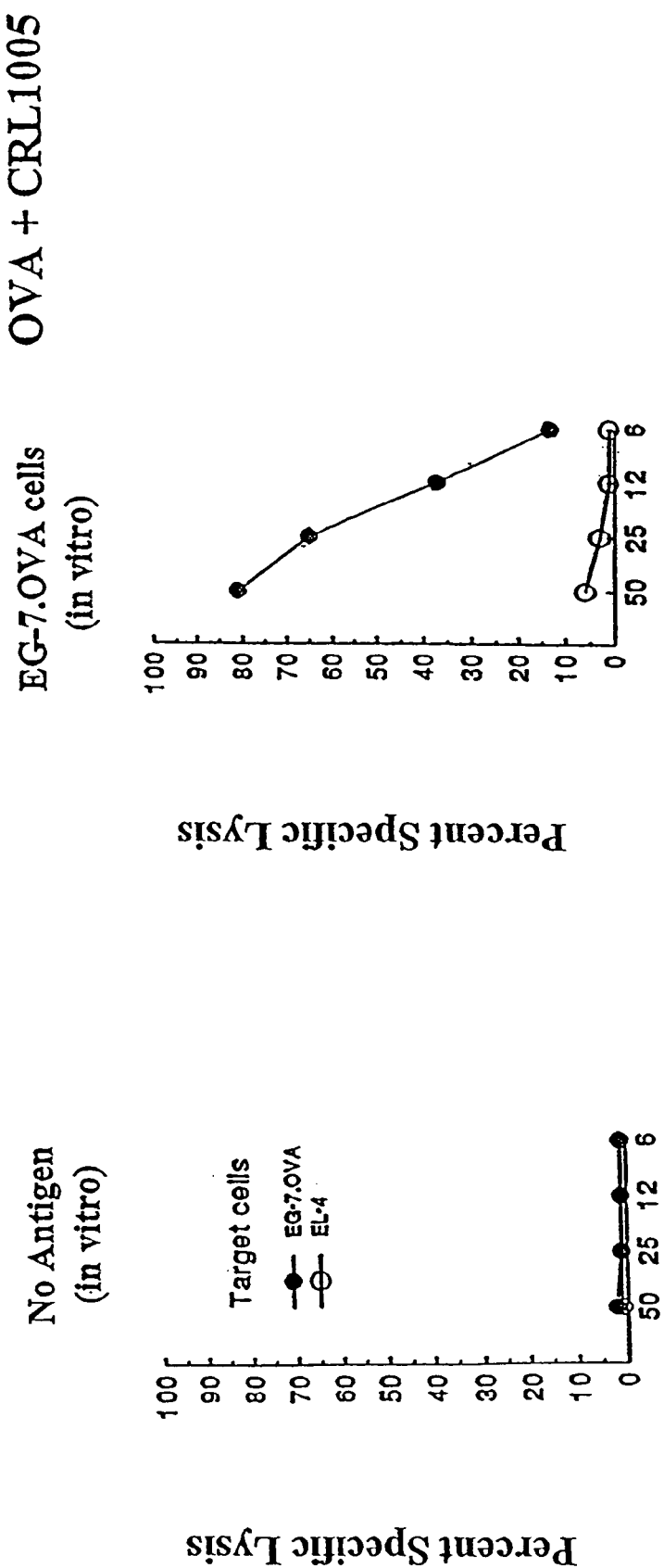

Results of the immunization are presented in FIG. 9. The quantity of HBsAg-specific antibodies detected in individual mouse sera is expressed as geometric mean titer. The animals that received a single injection of 0.5. µg HBsAg and 2.5 mg of CRL1005 had at least 4 times as much antibody against the HBsAg as did animals which received 0.5 µg of HBsAg in alum. The amount of alum which was included in the two formulations was equivalent to the accepted amount of alum in currently licensed and marketed recombinant hepatitis B vaccines. Also, the vaccine containing no CRL1005 was only marginally immunogenic, inducing barely detectable anti-HBsAg responses. None of the animals which were vaccinated with the 0.5 µg BBsAg in saline showed measurable antibody responses by day 28, as determined by those individuals having greater than 100 mIU/ml (Table 1). Because sera were diluted 1:10 for assay, a value less than 100 was considered below the cutoff for significance. A serum level of 10 mIU/ml is considered protective in humans, usually obtained on undiluted serum. 50% of the animals that received a single injection of HBsAg with CRL1005 induced measurable antibody responses to greater than 100 mIU/ml, whereas in only 25% of the animals were measurable antibody responses induced to the vaccine formulated with alum alone.

TABLE I

| | Seroconversion rates 28 days following a single injection of 0.5 µg HBsAg | | |
|---|---|---|---|
| Vaccine | a-HBsAG GMT | Seroconversion rate (percent) | Increase over control |
| 2.5% CRL1005 | 127 | 3/6 (50) | 4 |
| 0.25 mg alum (control) | 31 | 2/8 (25%) | 1 |
| No additions | 2 | 0/8 (0) | 0.06 |

EXAMPLE VII

Evaluation of Antigen-Specific Antibody and Cytokine Responses Induced Using Different Adjuvants and Suboptimal Dose of Ovalbumin A. Test Reagents, Animal Requirements and Experimental Design The immune responses induced by experimental subunit vaccine formulations based on a prototype immunogen combined with different adjuvants including CRL1005 were evaluated. Ovalbumin (OVA) was selected as to vaccine immunogen since dose levels of OVA for obtaining optimal and suboptimal immune responses had been established previously. In addition, OVA was selected because of the availability of a model to assess cytotoxic T-lymphocyte responses in C57BL/6 mice, based on the EG-7 OVA cell line (American Type Culture Collection, Rockville, Md.) (See Moore, et al., "Introduction of soluble protein into the class I pathway of antigen processing and presentation" *Cell* 54:777 (1988)) that is stably transformed with OVA and expresses OVA peptides associated with class I MHC antigens. OVA was administered at a dose of 15 ug/dose in a total volume of 100 ul. This dose of OVA had been established as non-immunogenic unless combined with an adjuvant.

Ninety mice (C57BL/6) were divided into 9 test and control groups of 10 mice per group. The mice were immunized twice with 28 days between immunizations. Vaccines were administered by needle injection subcutaneously (s.c.) in a total volume of 100 μ/dose. The groups of mice were immunized according to the following format: Group 1—vehicle control (phosphate buffered saline-PBS); Group 2—15 μg of the OVA in PBS; Group 3—15 μg of the OVA adsorbed to 125 μg of alum; Group 4—15 μg of the OVA formulated with CFA in a water-in-oil (W/O) emulsion, second immunization was given with incomplete Freund's aduvant; Group 5—15 μg of the OVA formulated with 20 μg Quil-A; Group 6—15 μg of OVA formulated in a W/O emulsion containing CRL1005, 2.5% concentration of 5 mg/200 μl dose; Group 7—15 μg of OVA formulated with Ribi adjuvant as an oil-in water (O/W) emulsion; Group 8—15 μg of the OVA formulated with CRL1005, 2.5% final concentration or 5 mg/200 μl dose; Group 9—15 μg of the OVA formulated with CRL1005, 5.0% final concentration or 10 mg/200 μl dose.

B. Measurement of Antigen-specific Immune Responses

To evaluate antibody responses, 4 weeks after the second immunization blood was collected via the retro-orbital sinus from 6 mice/group and sera was recovered for serological assay.

To evaluate cytokine responses, spleens were removed aseptically from the remaining 4 mice in each group and mononuclear cells recovered. Splenic mononuclear cells were cultured at a concentration of $4 \times 10^6$ cells/ml with or without 25 μg/ml OVA. Cultures were terminated and supernatant fluid collected at 4 hours, and at 1, 3 and 5 days. Cytokine concentrations were measured using an antigen-capture ELISA, based on commercially available antibodies. Cytokine concentrations in culture supernatants were determined using a standard curve and recombinant cytokines as the reference standard. The standard curve ranges were 30–2000 μg/ml. ELISAs for the measurement of IL-2, IL-3, IL-4, IL-5, IL-6, IL-10 and granulocyte-macrophage-colony stimulating factor (GM-CSF) were performed. For gamma interferon, the standard curve range was 150–10,000 pg/ml.

Cytotoxic T-lymphocyte responses (CTL) were measured using a standard in vitro assay and two different cells for stimulator and target cells. The OVA.EG7 cell line was used as both target cells and antigen specific stimulator cells; cells were irradiated when used as stimulator cells. Control target cells were wild-type EL-4 cells, that are not transfected with OVA. Splenic mononuclear cells were used as the effector cells. These cells were assayed after in vitro stimulation to induce precursor CTL maturation to functional CTL effector cells.

C. Results

1. Measurement of OVA-specific Antibody Responses:

OVA-specific antibody responses were not induced 4 weeks following two immunizations with 15 μg of OVA in saline, as shown in FIG. 10. However, high-titered antibody responses were induced using complete Freund's adjuvant, followed by incomplete Freund's adjuvant, and a W/O formulation containing the CRL1005 copolymer. These data demonstrate the poor immunogenicity of OVA when used at the selected dose without adjuvants and further demonstrate that this lack of immunogenicity can be corrected using potent adjuvants.

Evaluation of alum, Ribi O/W adjuvant and two concentrations of the aqueous particulate CRL1005 demonstrated that these 'clinically relevant' adjuvants could partially correct the lack of immunogenicity (FIG. 11). The alum-based formulation induced significant antibody responses in 1/6 mice whereas the Ribi formulation induced responses in 2/6 animals. The formulations containing 2.5% and 5.0% CRL1005 induced significant antibody responses in 3/6 and 4/6 mice, respectively. The Quil-A saponin adjuvant supplemented formulation did not induce significant antibody responses in any of the mice. These data demonstrate that the CRL1005 supplemented aqueous formulations are more immunogenic that those formulated with alum or Quil-A and are equal to or slightly better that the Ribi O/W formulation.

2. Measurement of Antigen-induced In Vitro Cytokine Production

Immunization with OVA alone did not induce measurable cytokine responses, similar to the result observed for antibodies. The analysis was then focused on the clinically relevant adjuvants, alum, saponin (Quil-A), Ribi O/W and CRL1005. None of these cytokines was detected in culture supernatants after only a 4 hour culture indicating that spleen cells from immunized mice were not constitutively producing large amounts of cytokines. Detectable levels were also not produced in vitro in response to antigenic stimulation with OVA at day 1 but were detectable at days 3 and 5 (Table 2).

TABLE 2

Measurement of cytokine production by splenic mononuclear cells from mice immunized with OVA and clinically relevant adjuvants.

| Cytokine Detected (day) | ADJUVANT USED | | | |
| --- | --- | --- | --- | --- |
| | Alum | Quil-A | Ribi (O/W) | CRL1005 (2.5%) |
| IL-2 (3) | — | — | — | 35 |
| IL-2 (5) | — | — | — | 93 |
| IL-3 (3) | — | — | — | — |
| IL-3 (5) | 73 | 83 | — | — |
| IL-4 (3) | — | — | — | — |
| IL-4 (5) | — | — | — | — |
| IL-5 (3) | 781 | 42 | — | 101 |
| IL-5 (5) | 971 | 1720 | 38 | 1234 |
| IL-6 (3) | — | — | 38 | — |
| IL-6 (5) | 100 | — | 160 | — |
| IL-10(5) | — | — | — | — |
| IL-10(5) | >2000 | 723 | — | 901 |
| GM-CSF (3) | 73 | 16 | 23 | 22 |
| GM-CSF (5) | 763 | 982 | 724 | 818 |
| γ-IFN | 95 | 316 | — | 371 |
| γ-IFN | 867 | 1749 | 880 | 1526 |

Data are expressed as pg/ml. The standard curve ranges for all cytokines, except γ-IFN, were 30–200 pg/ml. Data expressed as (—) represent readings less than the lowest value on the standard curve.

Cytokine production was readily detectable for groups of mice that did not produce detectable levels of serum antibodies specific for OVA, such as those immunized with Quil-A containing formulations. All of the adjuvants induced high levels of GM-CSF production whereas none appeared to induce IL-4 production and only low levels of IL-3 were produced. Only alum and Ribi adjuvants induced IL-6 products. Only those mice that received formulations containing the CRL1005 copolymer produced high levels of IL-2 and gamma interferon (γIFN) suggesting this adjuvant might be a more potent inducer of Type 1 cytokine responses. The use of higher concentrations of CRL1005 did not significantly increase the production of any of these cytokines.

3. Measurement of OVA-Specific CTL Responses

Mice immunized with OVA in saline without an adjuvant were tested to establish the background of the assay system. CTL activity against the EL-4 and EG-7. OVA target cells was not detected following culture of spleen cells without antigen or with irradiated EG-7.OVA. These results indicate that CTL activity specific to OVA was not induced by immunization with OVA in saline. Animals immunized with formulations containing the CRL1005 were tested in a similar manner. CTL specific for OVA were not detected following culture of spleen cells without antigen. However, CTL were readily detected after culture of spleen cells with the EG-7.OVA cell line. The CTL killed only the EG-7.OVA cells, not the EL-4 cells, which demonstrated their antigen specificity. Since the EG-7.OVA cells express only class I major histocompatibility complex (MHC) antigens, the CTL activity is assumed to be the function of CD8+ T-lymphocytes. These results demonstrate that CTL activity specific to OVA was induced by vaccination with OVA formulated with CRL1005 adjuvant in a simple aqueous solution.

The basis of the animal model was the selection of a dose of OVA that was non-immunogenic unless used with an adjuvant. Based on antibody responses, these studies demonstrated that the 15 μg/dose of OVA was apparently non-immunogenic when used alone but was very immunogenic when formulated with experimental W/O adjuvants. The adjuvants that are more likely to be used in vaccines, the 'clinically relevant' adjuvants, all augmented antibody responses but to a lesser degree. The CRL1005 polymer was more potent that saponin (Quil-A) and alum and at least equal in potency to the Ribi O/W adjuvant.

While not wanting to be bound by this statement, it is believed, based on the initial evaluation of cytokine production profiles, that the CRL1005 polymer induced both Type 1 and Type 2 responses since IL-2, γIFN, IL-5 and IL-10 were produced. Type 1 and 2 responses are defined based on the cytokines produced by lymphocytes responding to an antigen. The Type I cytokine profile is the production of interleukin (IL) 2 and γIFN. The Type 2 profile is the production of IL-4, IL-5, IL-6 and IL-10.

EXAMPLE VIII

Rabbit Toxicology Trial and Stability Experiments

The CRL1005 polymer and related polymers are synthetic and manufactured under GMP standards. Thus they represent a more consistent product that those derived from natural sources such as bacterial endotoxins and saponins. Rabbits have received three doses, administered intramuscularly, and no toxic reactions have been observed.

CRL1005 has been, and is continuing to be, evaluated to determine its stability. Currently, real-time stability data has been generated for both the CRL1005 polymer in bulk (1 year) and in aqueous formulation (7 months). Thus, this technology appears well suited for use in subunit vaccines.

EXAMPLE IX

Oral Delivery of Vaccines Containing Block Copolymer

The ability to deliver vaccine orally has two advantages over standard parenteral routes: (1) ease of administration and (2) the possibility of inducing mucosal immune responses. The large copolymers are well suited for use in vaccine formulations because (1) they are nonionic and therefore resistant to damage by stomach acids, (2) they inhibit lipase activity which should contribute to their utility with emulsions containing squalane, and (3) they can be used in aqueous formulations where they form appropriately sized particles.

The utility of the CRL1005 copolymer for use as an oral vaccine adjuvant/delivery system using OVA as the vaccine antigen was evaluated. To ensure immunogenicity of the formulation, C57BLJ6 mice in the positive control group were immunized twice, at ten day intervals, subcutaneously (s.c.) with 25 μg/100 μl dose of OVA+/−1.25% CRL1005 in PBS. Mice immunized orally received 125 μg/500 μl dose of +/−1.25% CRL1005 in bicarbonate buffer, again at 10 day intervals. Mice were also immunized using nasal delivery since dilution or degradation in the stomach was considered to be a possibility. Mice received the same amounts of OVA and CRL1005 used for the s c injections but in a volume of 20 μl. Blood was collected as the source of serum antibodies for testing 14 days after the second immunization.

Figures 13D, 13E, 13F:
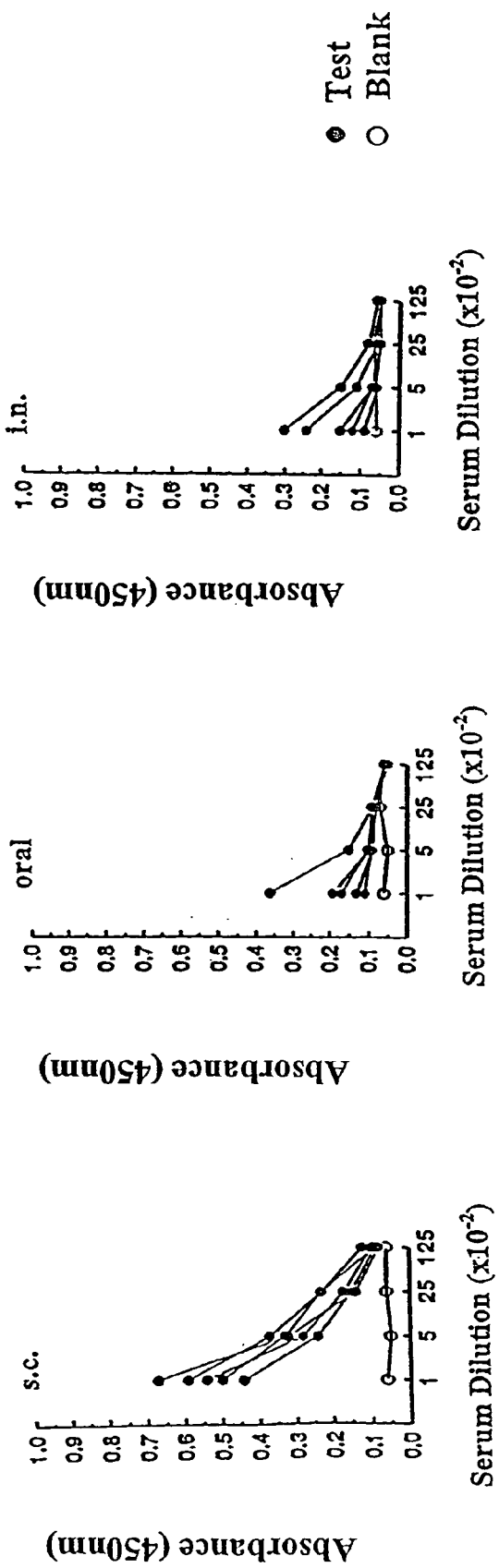
FIG. 13 shows serum antibody responses to OVA in C57BLJ6 mice following two immunizations with OVA administered s.c. orally or nasally without CRL1005 (upper) or with CRL1005 (lower). Sera from five animals per group were evaluated using a standard ELISA and a $\log_5$ titration of sera ($1/100$–$1/12,500$). All testing was done in duplicate. Data are shown as the mean absorbance (450 nm) for each serum dilution for individual mice (●—●). The background for the ELISA was established by omission of the mouse serum(o—o).

The results of this study are shown in FIG. 13. Oral or nasal immunization with OVA alone failed to induce antibody responses detectable using serum although s.c. immunization was effective. The addition of CRL1005 to the formulations increased the immunogenicity of the s.c. formulation and induced serum antibodies following both oral and nasal dose routes. These data demonstrate the utility of the CRL1005 copolymer in vaccines to be delivered orally or nasally.

EXAMPLE X

This example demonstrates the effect of the certain of the copolymers of the present invention on gene transfer into mammalian cells.

Cells and reagents: Chinese hamster ovary cells (CHO-K1) and COS-7 African green monkey kidney cells were obtained from ATCC, Rockville, Md. Cell culture media (Ham's F-12 medium, Dulbeccos Modified Eagle's Medium), Hanks Balanced Salts, antibiotics (Penicillin-Streptomycin) and β-galactosidase substrate X-Gal (5-bromo-4-chloro-3-indolyl-β-D-galactoside) were obtained from Sigma, St. Louis, Mo. Fetal calf serum was obtained from Gibco-BRL, Grand Island, N.Y. and Atlanta Biologicals, Atlanta, Ga. Lipofectin and Opti-MEM were obtained from Gibco BRL, Grand Island, N.Y. DOTAP was obtained from Boehringer Mannheim, Indianapolis, Ind. β-galactosidase plasmid pCMVβ (7.2 kb) was obtained from Clontech, Palo Alto, Calif., pSVβ (6.74 kb) was obtained from Promega, Madison, Wis. pATCgD plasmid encoding HSV-1 glycoprotein D was obtained from Dr. Kousoulas, LSU, Baton Rouge, La.

Poloxamers: Non-ionic block copolymers (poloxamers) were synthesized at CytRx Corporation, Norcross, Ga. and stored in crystalline form at room temperature. Poloxamer compounds CRL-1012, CRL-1029, CRL-1190, CRL-1005, CRL-1023 and CRL-1030 were resuspended in sterile water at a concentration of 10–20 mg/ml and stored in sealed bottles under nitrogen and at 4° C. These were diluted in tissue culture medium before adding them to cell cultures.

In vitro Transfection with Liposomes: CHO and COS-7 cells were plated on 24-well Costar plates, approximately $1 \times 10^5$ in 1.0 ml of medium and incubated at 37° C. in a 5% $CO_2$ incubator. Cells were grown to 50% confluency and transfected with β-gal plasmids using as transfection reagents either Lipofectin, DOTAP or poloxamers.

Transfection with Lipofectin was done as follows: Cell were washed twice with low-serum medium (Opti-MEM), then the transfection mixture (200 μl of Opti-MEM at 37° C., 2 μl of Lipofectin and 1–2 μg of plasmid DNA, mixed in a polystyrene tube) was added and the cells were incubated for 6 hrs at 37° C. in 5% $CO_2$. Following incubation, the transfection mixture was removed by aspiration, fresh DMEM-10% FCS (0.8 ml) was added, and the cells were further incubated for 48 hrs. Transfections with DOTAP were done in a similar way with the difference that transfection mixtures contained DMEM plus 10% FCS instead of low-serum medium Opti-MEM.

In vitro Transfection with Poloxamers: CytRx poloxamers CRL-1012, CRL-1029, CRL-1190, CRL-1005, CRL-1023 and CRL-1030 were screened for their ability to transfect DNA into mammalian cells in vitro using a method based on the method described for liposome-mediated DNA transfection. To optimize this method for efficient transfection the following conditions were tested: mixing DNA (2 μg) with poloxamers at a wide range of concentrations (5 μg/ml to 50 mg/ml); mixing DNA and poloxamer in water, buffers (PBS, Tris, HBS), at various pH (5–7.5); addition of $MgCl_2$ (1–50 mM); mixing DNA and poloxamer at various temperatures (0–4° C., 25° C.–37° C., temperature shifts 4° C. to 37° C.); mixing by vortexing, sonication or syringe emulsification; presence of serum in transfection mixtures; transfection of cells at different confluencies (20%, 590%), times (6 hr, 24 hr); and rotation of plates during transfection.

After extensive studies to find the optimal conditions for in vitro transfection with poloxamers, the following protocol was adopted. The transfection mixture was prepared in ice and consisted of 1 μl of plasmid DNA (2 μg), 18 μl of poloxamer suspension in water (50–200 μg/ml) for a total of 20 μL. The poloxamer-DNA mixture was incubated in ice for 15 minutes, shifted to 37° C. and incubated for 5 minutes. After 3 temperature shifts from 4° C. to 37° C., 180 μl of DMEM-10% FCS were added and the mixture (200 μl) was added to the cell monolayer at 50–60% confluency and the cells incubated for 24 hrs at 37° C. in 5% $CO_2$. Following incubation, the transfection mixture was removed by aspiration, fresh DMEM-10% FCS (1 ml) was added, and the cells were further incubated for 48 hrs.

X-Gal Staining of transfected cells: COS-7 and CHO cells transfected with β-galactosidase plasmids were tested after 48 hrs for expression of β-galactosidase by staining with the substrate X-Gal. The medium was removed and gently the cell monolayer was washed 2 times with PBS, pH 7.3 (calcium and magnesium free). Cells were fixed for 30 min. at 37° C. in 1 % formaldehyde in PBS (0.5 ml/well) and washed 2 times in PBS (1 ml/well). Added 200 μl of X-Gal staining solution (800 μg/ml X-Gal in dimethylformamide, 4 mM potassium ferrocyanide, 4 mM potassium ferricyanide, 2 mM $MgCl_2$ in PBS, pH 7.3) and incubated the cells for 24 hrs at room temperature. After staining, the plates were washed 2 times in PBS, 2% formaldehyde in PBS was added (1 ml/well) and observed under the microscope for counting the number of cells stained dark blue.

Genetic Immunization and HSV ocular Infection: BALB/c 5–7 week old female mice (4 per group) were immunized either i.p. or i.m. with pATCgD plasmid alone (20 μg or 50 μg), pATCgD (20 μg) plus DOTAP (50 μg or 100 μg), and pATCgD (10 μg, 20 μg or 50 μg) plus CRL-1012 (50 μg, 200 μg or 1 mg). Animals immunized i.p. received one inoculation of 200 μl; animals immunized i.m. received one inoculation (100 μl per leg) into both quadriceps. Animals received two inoculations every two weeks and serum samples were collected two weeks after each inoculation. Two weeks after the last inoculation animals were infected with HSV-1 by scratching the corneal epithelium of one eye with a 25-gauge needle (6 crisscross strokes) and by applying the virus suspension ($1.6 \times 10^6$ pfu/ml) with a cotton-tipped applicator. Animals were examined under a microscope 2–3 times a week for two weeks post-infection and once a week thereafter. The eyes were graded on a scale 0 to +4 for blepharitis, stromal keratitis and vascularization. The results were expressed as severity of disease, % morbidity and % mortality.

Genetic Immunization and HSV skin infection: SKH-1 hairless mice (5–7 week old females) were immunized i.m. with pATCgD plasmid alone (20 μg or 50 μg), pATCgD (20 μg) plus DOTAP (50 μg or 100 μg), and pATCgD (20 μg or 50 μg) plus CRL-1012 (50 μg or 200 μg). Each treatment group included 4 mice. Animals received two inoculations animals (100 μl per leg) into both quadriceps every two weeks and serum samples were collected two weeks after each inoculation. Two weeks after the last inoculation animals were infected with HSV-1 by scratching the skin at the base of the neck (1 cm) with a 25-gauge needle and by rubbing the scarified skin site with a cotton-tipped applicator dipped in a virus suspension ($1.0 \times 10^{11}$ pfu/ml). Each group of animals were examined two times a week for two weeks and scored for size of the lesion (0 to 4), % morbidity and % mortality.

Antibody Screening by Indirect Immunofluorescence and ELISA: Sera from animals immunized with pATCgD plasmid alone or in combination with poloxamers were tested for specific antibody response to HSV gD by indirect immunofluoresence (IIF) and ELISA. IIF was done with CHO cells transiently expressing HSV gD at the cell surface after transfection with pATCgD and DOTAP (as described previously). Transfected cell monolayers (in 8-well chamber slides) were incubated for 72 hrs to allow for maximum cell surface expression of HSV gD. Cell monolayers were washed twice in PBS, fixed in 1% formaldehyde in PBS and permeablized in methanol at −20° C. for 3 minutes. Cells were washed in PBS and incubated in blocking buffer (1% FCS in PBS) for 30 minutes at room temperature. Cells were washed 3 times in PBS and incubated (1 hr at room temp.) with sera from immunized animals diluted 1:100 in blocking buffer. Cells were washed 3 times in PBS and incubated for 1 hr at room temp. in antibody conjugate (rabbit anti-mouse IgG FFITC) diluted 1:1000 in blocking buffer. Following labeling, the slides were washed in PBS, covered with a cover slip in mounting media and examined by fluorescence microscopy.

Antibody screening by ELISA was as follows: Vero cells cultured in T flasks (75 $cm^2$) were infected with HSV-1 (MOI of 5–10) and after 24 hrs harvested from the culture flasks and washed twice in PBS by centrifugation. The pellet of infected cells was resuspended in 10 ml of PBS and the cell suspension transferred to 96-well microtiter plates (50 μl/well). The cell suspension was allowed to dry for 24 hrs, fixed with methanol for 20 minutes and washed with PBS. Coated plates were stored at −20° C. until used. Sera from immunized animals were tested at 1:50 to 1:1000 dilutions in PBS/0.05% Tween-20 (PBST), and the secondary antibody consisted of goat anti-mouse IgG-HRP at 1:500 to 1:1000 in PBST. The color-producing substrate solution (40 mg o-phenylenediamine, 0.05% $H_2O_2$ in citrate phosphate buffer) was incubated for 30 minutes and the reaction was stopped by addition of 25 μl of 8N $H_2SO_4$. The absorbance at 495 nm of each well was measured in a Molecular Devices SpectraMax 250 microplate reader.

Figure 14:
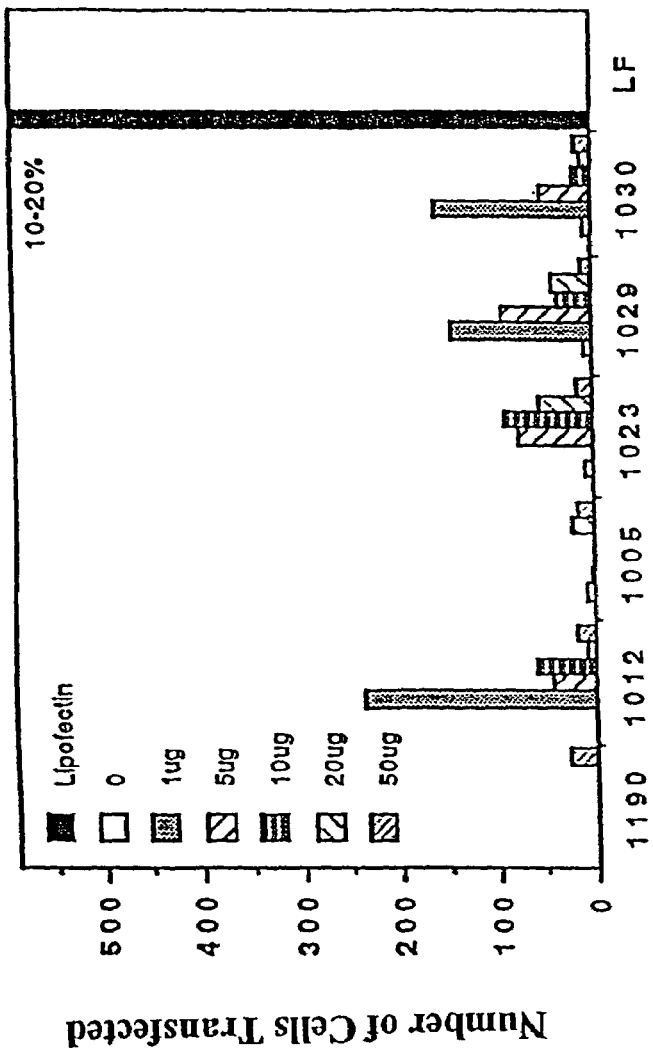
FIG. 14 shows the initial screening of poloxamers using a transfection method described for liposome-mediated DNA transfection.
Figure 15:
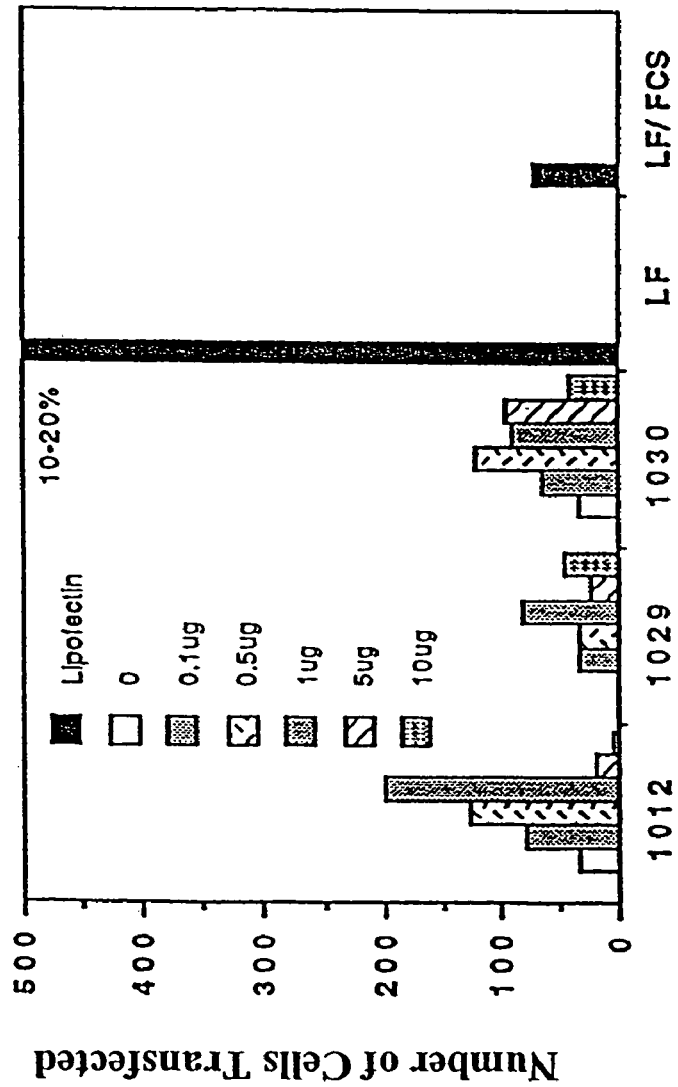
FIG. 15 shows transfection using poloxamers 1012, 1029 and 1030.

In vitro Transfection with Poloxamers: A series of poloxamer compounds were tested, under different conditions, for in vitro transfection of β-galactosidase reporter genes (pCMVβ or pSVβ) into mammalian cells. Initial screening of poloxamers was done following a transfection method based on the method described for liposome-mediated DNA transfection. Under these conditions it was shown that poloxamers CRL-1012, 1023, 1029 and 1030, at a concentration of 5 µg/ml, gave positive transfection, although the transfection efficiency was low (<1%) compared to the levels of transfection typically obtained with the commercial reagent Lipofectin (10–20%) in low serum medium (FIG. 14). Since DNA transfection by Lipofectin is inhibited by serum in the culture medium, it was decided to test poloxamers in the presence of medium containing 10% fetal bovine serum. Poloxamers 1012, 1029 and 1030 were shown to mediate DNA transfection at low levels (<1%) while transfection with Lipofectin was strongly inhibited by serum (FIG. 15).

Figure 16:
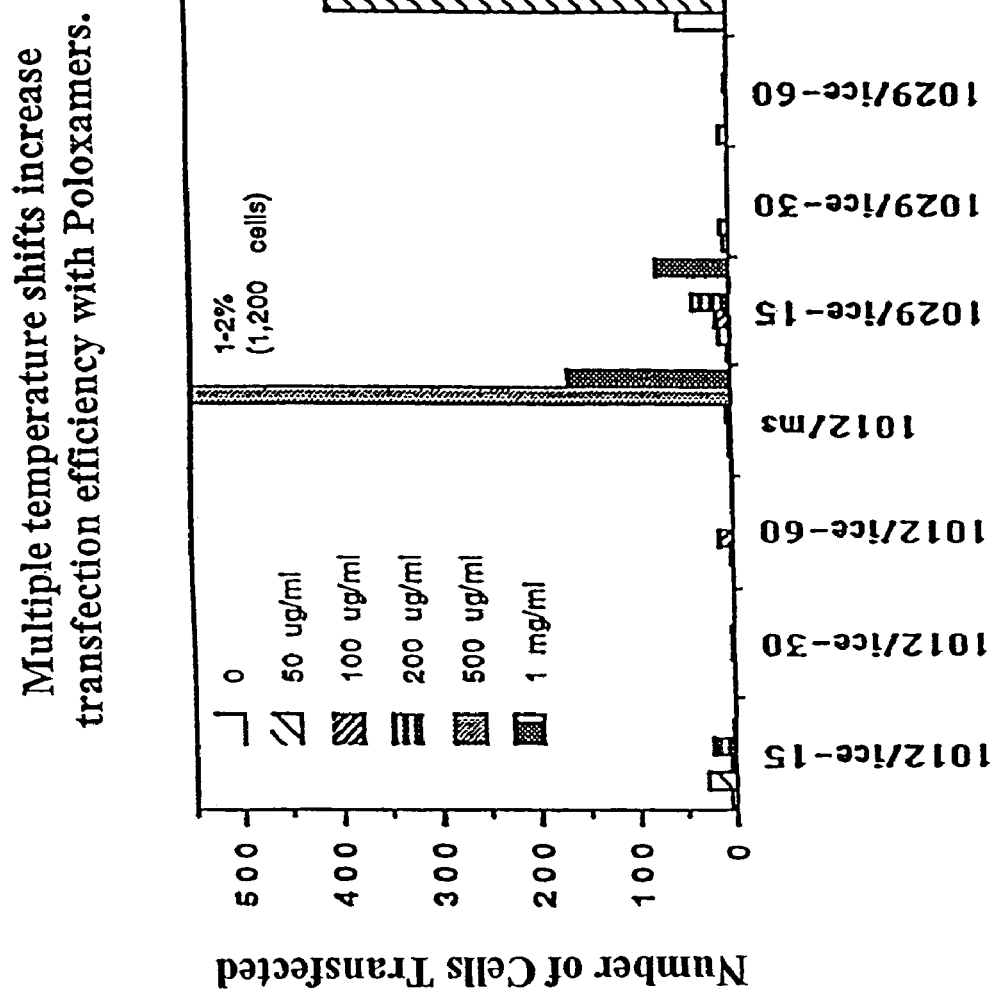
FIG. 16 shows the effect of temperature on transfection efficiency.
Figure 17:
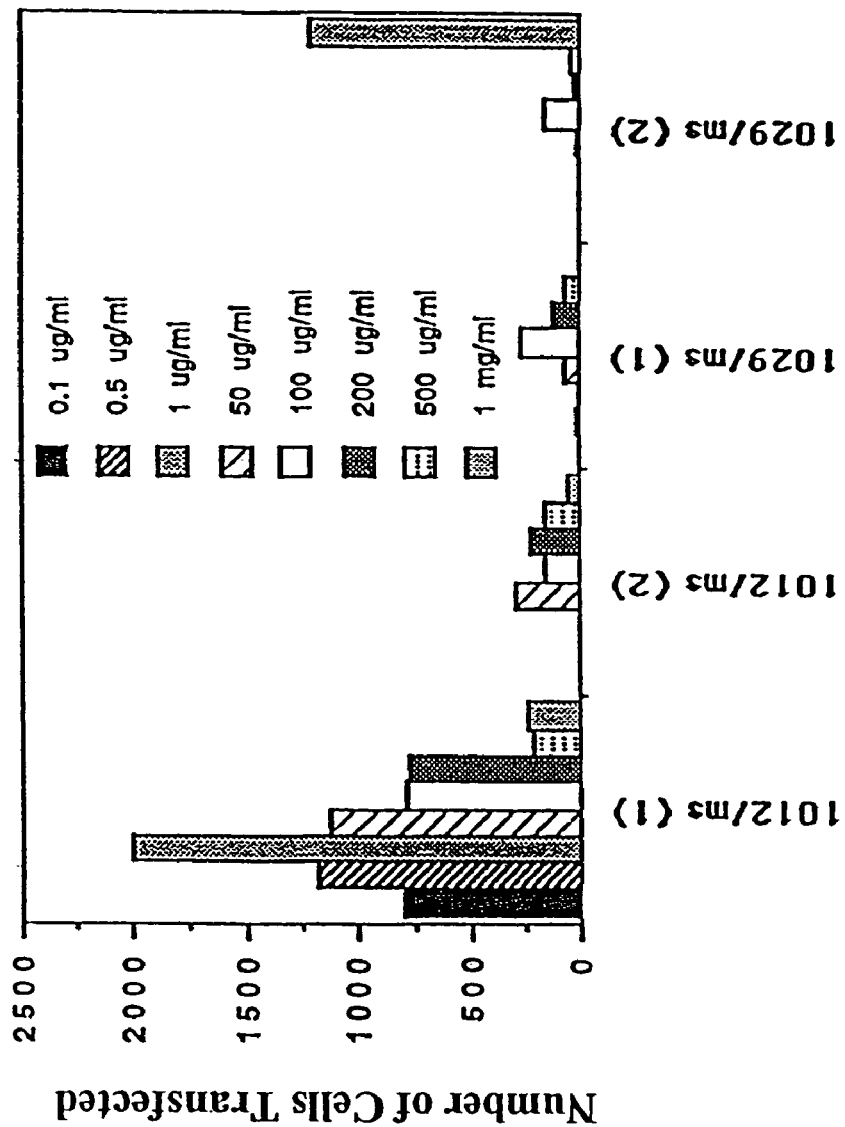
FIG. 17 shows the variability between poloxamer concentration and transfection efficiency.

Further testing and screening of poloxamer compounds for in vitro DNA transfer focused on compounds CRL-1012 and CRL-1029. A number of conditions were tested in order to improve the efficiency of transfection (see materials and methods). It was found that by mixing plasmid DNA (1–2 µg) and poloxamers (5–50 µg/ml) in ice (2° C.) and repeated temperature shifts from 2° C. to 25° C., the transfection efficiency was increased to levels of approximately 2–5% (FIG. 16). These poloxamers are water soluble at low temperatures presumably due to the formation of hydrogen bonds between water molecules and ether-linked oxygen groups in the POP block. At room temperature, or above the cloud point, poloxamers turn insoluble forming particulate aggregates. Although not wanting to be bound by the following theory, it is believed that during this phase transition DNA molecules are trapped into these aggregates which can be internalized by cells. In these studies, high variability was observed in duplicate experiments and no correlation could be established between poloxamer concentration and transfection efficiency (FIG. 17).

Figure 18:
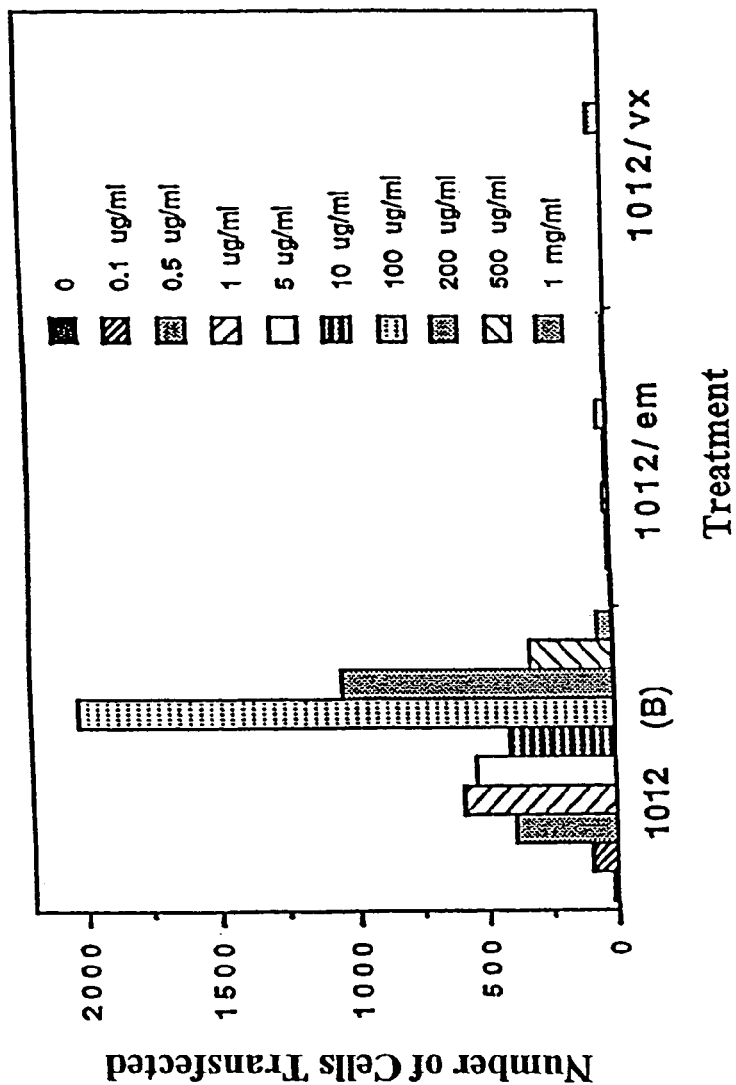
FIG. 18 shows the effect of mixing the poloxamer-DNA mixtures by vortexing or emulsification with a syringe.
Figure 19:
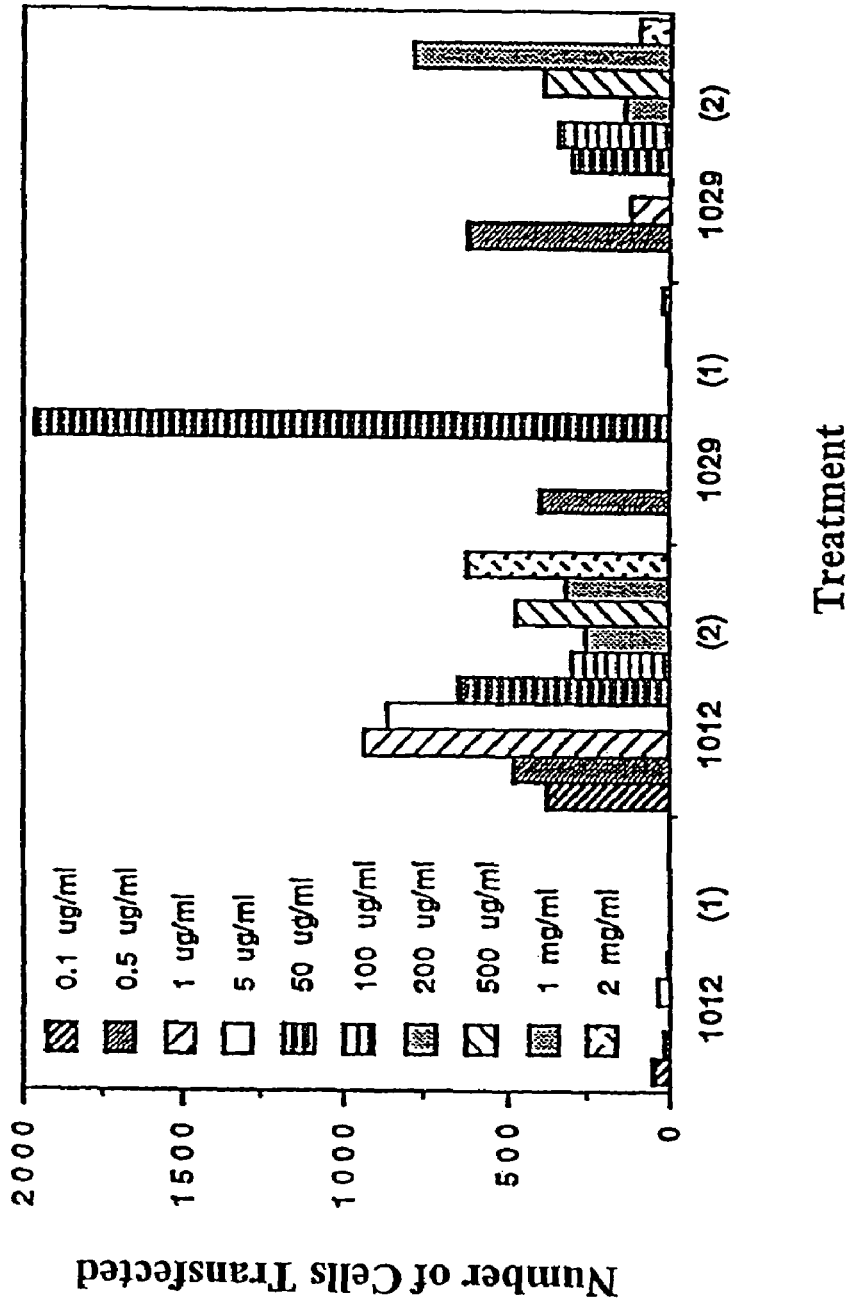
FIG. 19 shows the effect of rotating the plates for 24 hours during the transfection.
Figure 20:
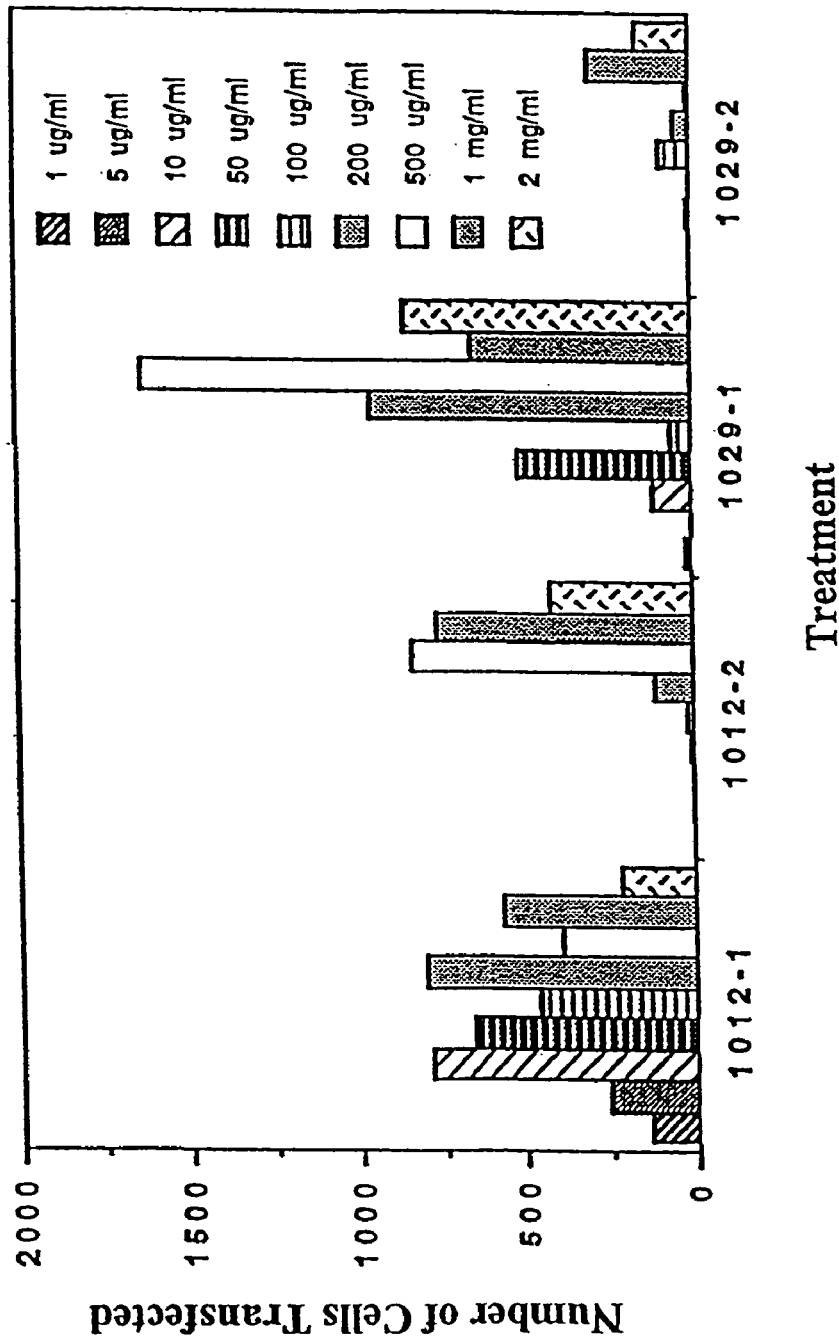
FIG. 20 shows the effect scaling up the assay conditions on efficiency of transfection.

It is possible that the formation of poloxamer-DNA aggregates is not very efficient and that these aggregates are unstable due to the non-ionic nature of poloxamers. It is also possible that under the conditions tested, poloxamer-DNA aggregates are not efficiently internalized by cells. It was found that mixing of poloxamer-DNA mixtures by vortexing or emulsification with a syringe, resulted in loss of DNA transfection activity (FIG. 18). Adding poloxamer-DNA mixtures to cells and rotating the plates for 24 hrs during the transfection was tested. Under those conditions, a slight enhancement of transfection was observed (FIG. 19). DNA transfections in larger volumes (6-well plates; 400 µl per well) was tested to determine if by scaling-up the assay conditions, the efficiency of transfection could be increased. The results showed that although the reproducibility of the assay was slightly improved, transfection efficiency was not increased (FIG. 20).

In summary, these results indicate that in vitro DNA transfection with poloxamers CRL-1012 and CRL-1029, under the conditions tested, result in transfection efficiencies of 2–5%. In comparison to commercial reagents, poloxamers gave transfection levels higher than Lipofectin (>1%) in the presence of serum, but lower than those obtained with DOTAP (20–30%) in serum This is shown in the following Table.

| Screening of CytRx Poloxamers for In vitro Transfection | |
|---|---|
| Poloxamer tested | Estimated % Transfection |
| 1005 | neg |
| 1012 | 2–5% |
| 1023 | <1% |
| 1027 | neg |
| 1028 | 1–2% |
| 1029 | 2–5% |
| 1030 | <1% |
| 1183 | neg |
| 1190 | <1% |
| 8131 | neg |
| Lipofection Controls | |
| Lipofectin | 10–20% |
| Lipofectin + FCS | <1% |
| DOTAP + FCS | 20–30% |

Further analysis is needed to define the optimal conditions and mechanism by which poloxamers mediate DNA uptake. It is possible that poloxamer-DNA complexes are taken-up by cells or that poloxamers increase cell membrane permeability allowing the uptake of DNA. Our data supports the idea that poloxamers form aggregates entrapping DNA and that these aggregates are internalized by cells. If poloxamer particles are taken-up by cells it would be of interest to develop these compounds as delivery vehicles for many different applications. Development of poloxamers for DNA delivery may require modification of poloxamers by addition of positively charged groups such as quaternary amino groups or conjugation to positively charged polylysine peptides. Positively charged poloxamers would bind DNA molecules through ionic interactions resulting in the formation of more stable complexes for delivery to cells. In addition, poloxamers linked to specific receptor ligands could be utilized for delivery of DNA to target specific organs and tissues by receptor mediated endocytosis.

In vivo Gene Vaccination Studies: Antibody responses to HSV-1 glycoprotein D: Initial studies tested the effect of poloxamer 1012 in genetic vaccination with the plasmid pATCgD (pgD). BALB/c mice (4 per group) were immunized either i.p. or i.m. with pgD plasmid alone, in combination with liposomes (DOTAP) or in combination with poloxamer 1012.

Figure 21:
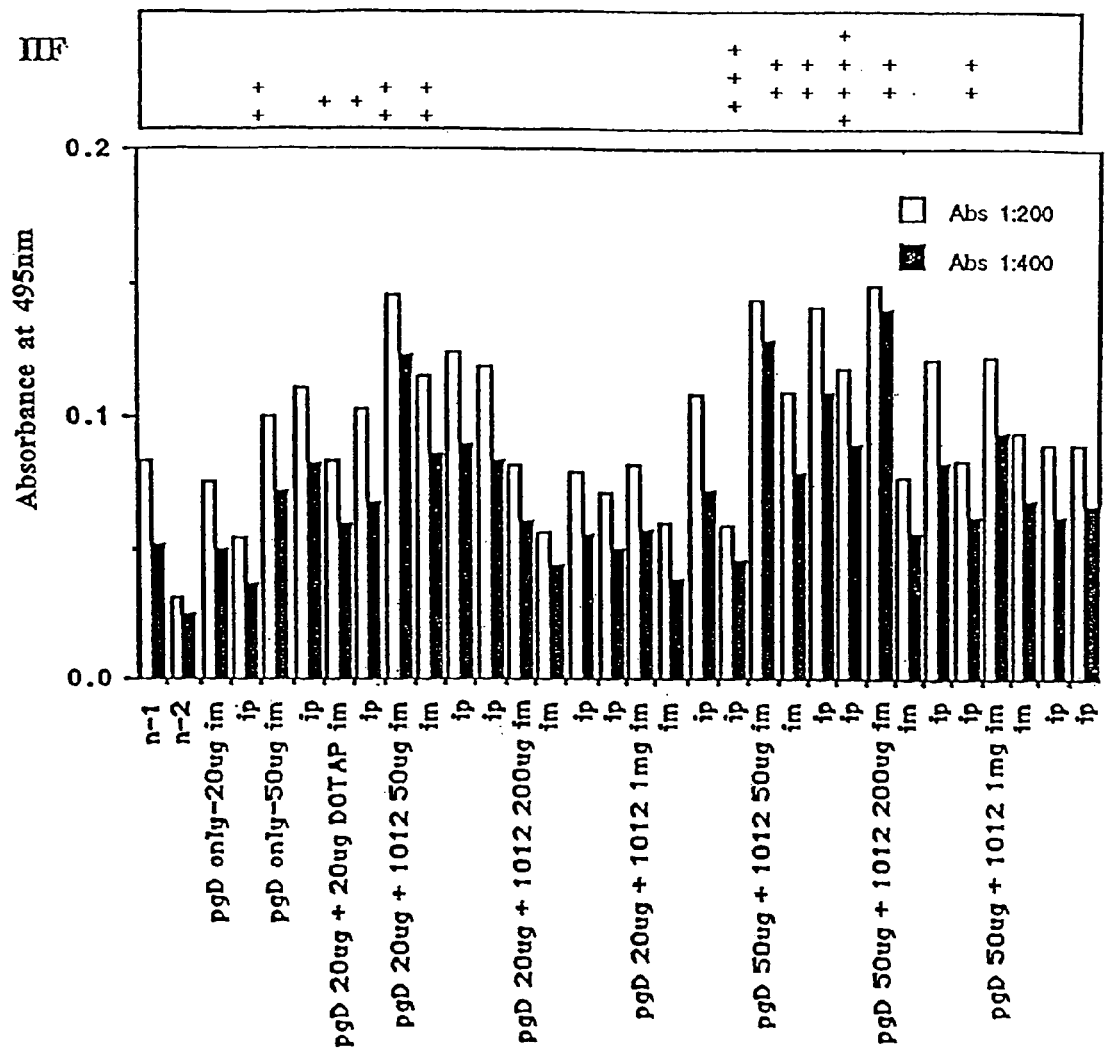
FIG. 21 shows the antibody response to genetic vaccination with pATCgD plasmid DNA.

After two inoculations every two weeks mice immunized with a mixture of pgD plus 1012 at different concentrations (pgD 20 µg/1012 50 µg, pgD 50 µg/1012 50 µg, and pgD 50 µg/1012 200 µg) showed positive anti-gD responses by IIF. The best antibody responses were obtained in animals inoculated intramuscularly (FIG. 21). The results obtained by IEF correlated with antibody titers obtained by ELISA. At serum dilutions of 1:200 and 1:400, the highest anti-gD responses were seen in animals immunized with mixtures of pgD and 1012 (FIG. 21). These results suggest that 1012 increases the efficacy of gene vaccination with pgD, by enhancing the uptake of DNA and or by acting as an adjuvant to potentiate the immune response.

Figure 22:
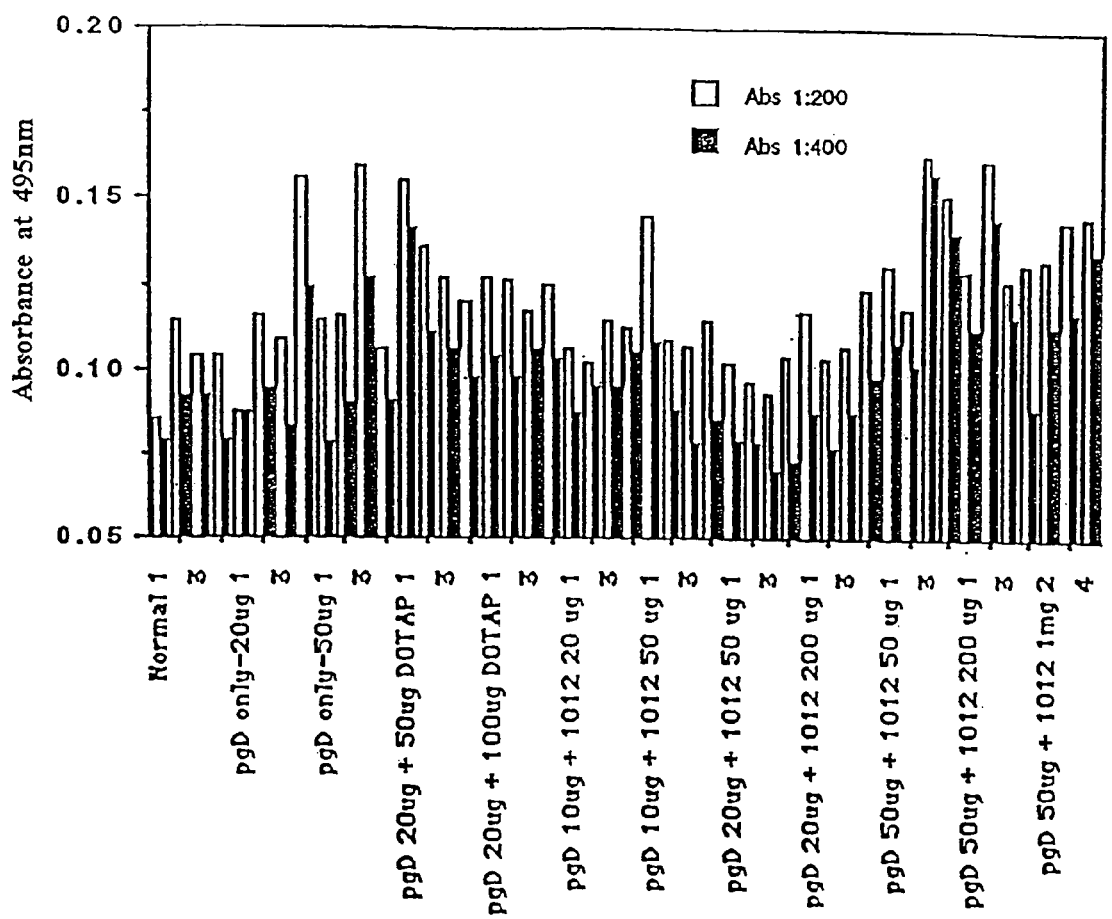
FIG. 22 shows the antibody response to genetic vaccination with pATCgD plasmid DNA prior to ocular infection with HSV-1.

Genetic vaccination against ocular HSV-1 infection: BALB/c mice (4 per group) were inoculated i.m. with pgD plasmid alone, in combination with liposomes (DOTAP) or in combination with poloxamer CRL-1012. After two inoculations every two weeks mice immunized with a mixture of pgD (50 μg)/1012 (50 μg, 200 μg and 1 mg) and animals immunized with a mixture of pgD (20 μg)/DOTAP (50 μg) showed higher anti-gD responses compared to groups immunized with pgD plasmid alone and mixtures of pgD/1012 at lower concentrations (FIG. 22).

Figure 23:
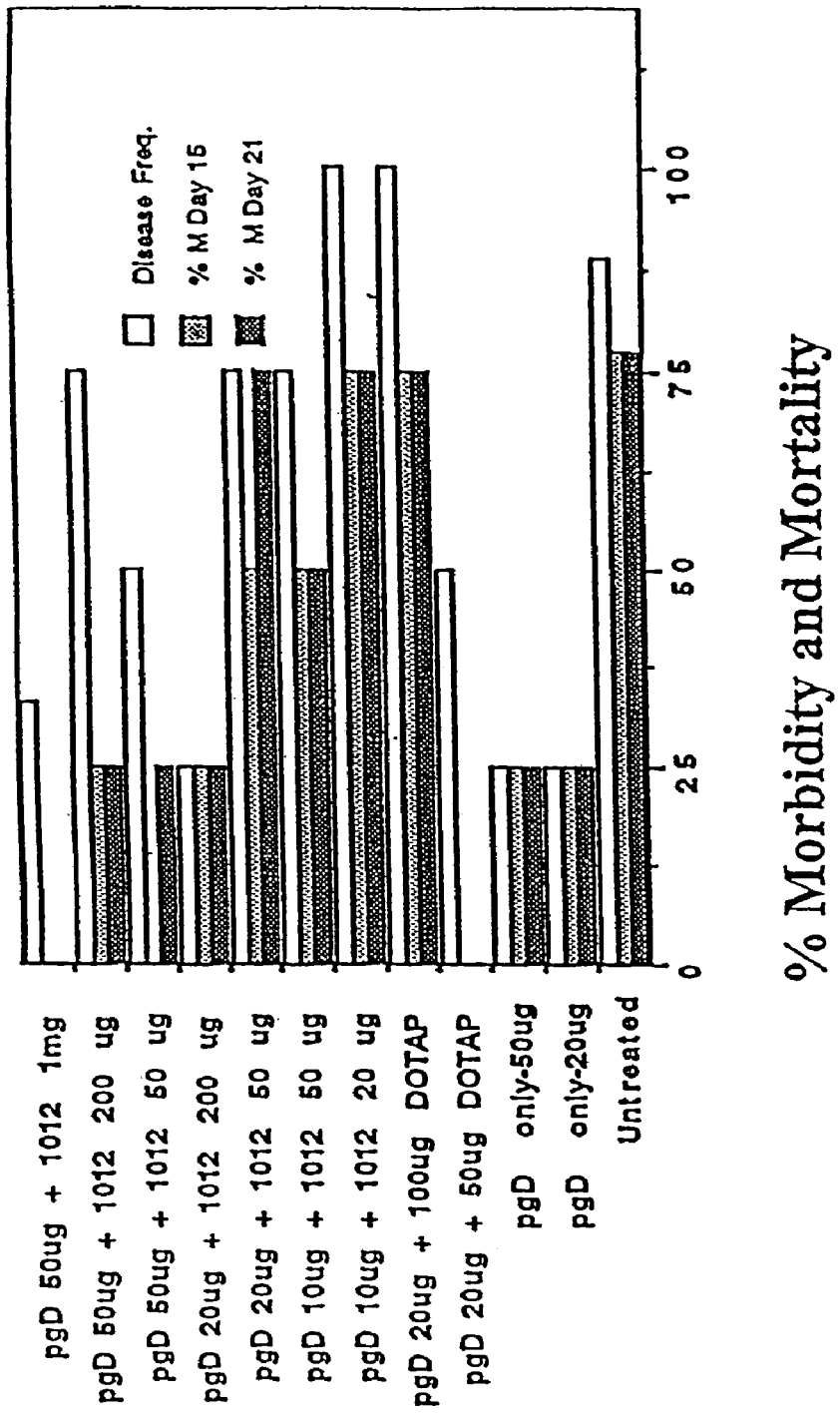
FIG. 23 shows genetic vaccination against ocular HSV-1 in BALB/c mice.

The efficacy of genetic vaccination with pgD and 1012 was tested by infecting animals through the corneal epithelium with HSV-1. Ocular infection of naive mice resulted in high morbidity (88%) and mortality (77%) during 15 days post-infection. The lowest morbidity rate was observed in animals immunized with pgD alone (20–50 μg) and animals immunized with pgD (20 μg) plus 1012 (200 μg, 1 mg). No mortality was observed in animals immunized with pgD (20 μg)/DOTAP (50 μg) and animals immunized with pgD (50 μg)/1012 (1 mg). Groups of mice immunized with pgD (50 μg)/1012 (50, 200 or 1 mg) showed high morbidity but only one mouse died (25%) of HSV infection (FIG. 23). In these experiments a positive correlation was observed between anti-gD antibody titers obtained by ELISA and % morbidity and mortality after a challenge infection with HSV-1.

Figure 24:
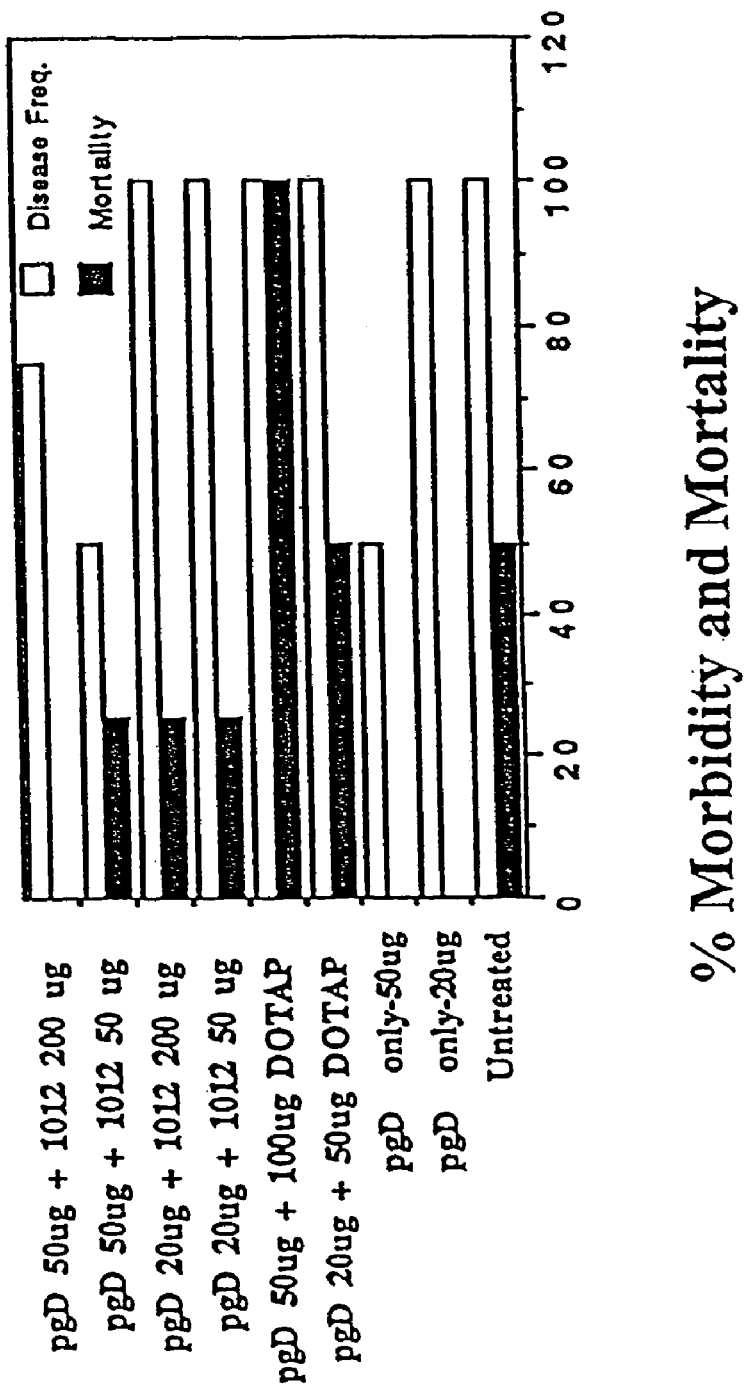
FIG. 24 shows genetic vaccination against HSV-1 skin infection in SKH-1 (Hairless) mice.
Figure 25:
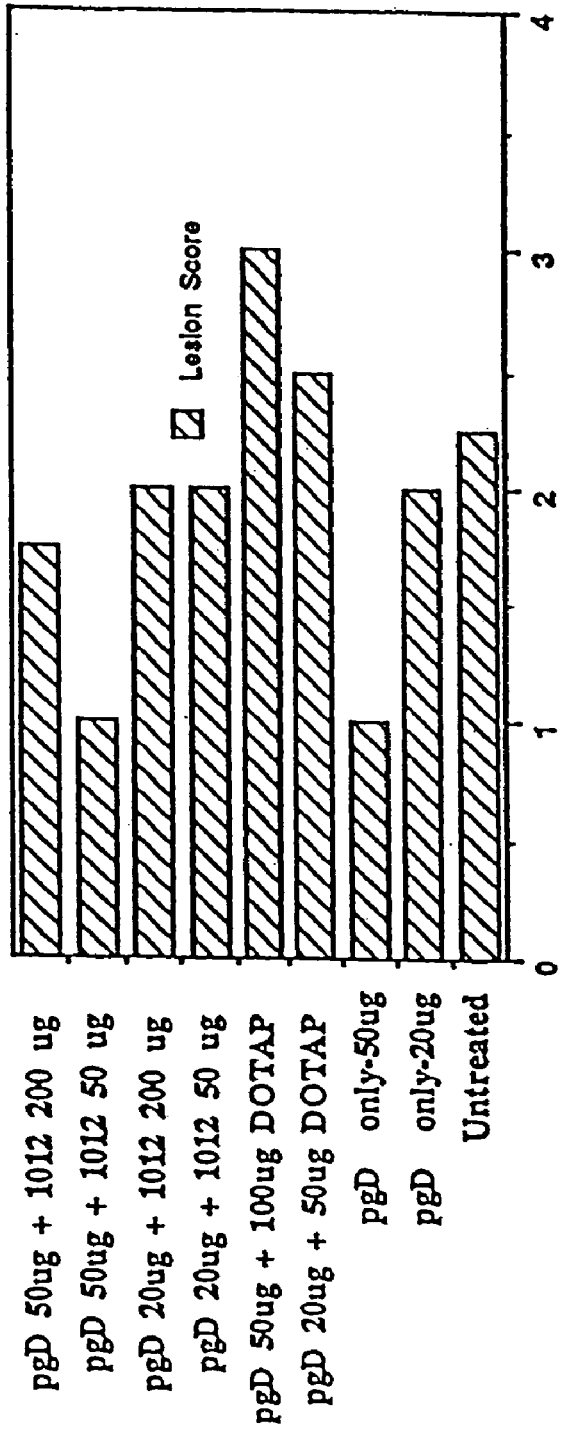
FIG. 25 shows the severity of HSV infection in SKH-1 (Hairless) mice after genetic immunization.

Genetic vaccination against skin HSV-1 infection in hairless mice: SKH-1 hairless mice immunized i.m. with pgD plasmid alone, in combination with DOTAP, or in combination with poloxamer 1012, and tested for immunity against a skin infection with HSV-1. Infection of naive mice resulted in 100% morbidity and 50% mortality during the first 15 days post-infection. Animals immunized with pgD alone (20 or 50 μg) showed high morbidity and no mortality. Animals immunized with pgD 20 μg/1012 200 μg and pgD 50 μg/1012 50μg showed 100% morbidity but only one mouse died (25%) from HSV infection. Animals immunized with pgD (50 μg)/1012 200 μg showed 80% morbidity but no mortality. The worse disease observed was in animals immunized with pgD (50 μg) plus DOTAP (100 μg), showing 100% mortality. Only in this group of animals systemic HSV disease was observed (FIG. 24). The severity of the disease was also assessed by scoring the size of the lesions (0 to 4). Less severe lesions, such as redness of the skin at the site of infection, were seen in animals immunized with pgD alone (50 μg) and animals immunized with pgD (50 μg)/1012 (50 μg) (FIG. 25).

It should be understood, of course, that the foregoing relates only to preferred embodiments of the present invention and that numerous modifications or alterations may be made therein without departing from the spirit and the scope of the invention as set forth in the appended claims.

The invention claimed is:

1. A composition comprising a compound admixed with a nonionic block copolymer having the following formula:

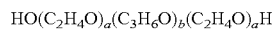

wherein "b" represents a number such that the molecular weight of the hydrophobe ($C_3H_6O$) is greater than 15,000 Daltons, and "a" represents a number such that the percentage of hydrophile ($C_2H_4O$) is between approximately 1% and 40% by weight;

wherein the compound admixed with the nonionic block copolymer is capable of altering gene activity.

2. The composition of claim 1, wherein "b" represents a number such that the molecular weight of the hydrophobe ($C_3H_6O$) is between approximately 15,000 and approximately 20,000 Daltons.

3. The composition of claim 1, wherein the percentage of the hydrophile ($C_2H_4O$) is between 2% and 25% by weight.

4. The composition of claim 1, wherein the nonionic block copolymer is substantially free of unsaturation.

5. The composition of claim 1, wherein the composition further comprises approximately 0.1% to approximately 5% by weight of a surfactant.

6. The composition of claim 1, wherein the composition further comprises approximately 0.5% to approximately 5% by volume of an alcohol.

* * * * *